US009309537B2

United States Patent
Ochiya et al.

(10) Patent No.: US 9,309,537 B2
(45) Date of Patent: Apr. 12, 2016

(54) CHIMERIC RAT PRODUCED USING RAT EMBRYONIC STEM CELLS IN THE PRESENCE OF AN ES CELL DIFFERENTIATION SUPPRESSANT

(75) Inventors: Takahiro Ochiya, Tokyo (JP); Masaki Kawamata, Tokyo (JP)

(73) Assignees: National Cancer Center, Tokyo (JP); DS Pharma Biomedical Co., Ltd., Suita (JP)

( * ) Notice: Subject to any disclaimer, the term of this patent is extended or adjusted under 35 U.S.C. 154(b) by 553 days.

(21) Appl. No.: 13/513,100

(22) PCT Filed: Nov. 30, 2010

(86) PCT No.: PCT/JP2010/071412
§ 371 (c)(1),
(2), (4) Date: Jul. 13, 2012

(87) PCT Pub. No.: WO2011/068103
PCT Pub. Date: Jun. 9, 2011

(65) Prior Publication Data
US 2012/0272349 A1    Oct. 25, 2012

(30) Foreign Application Priority Data

Dec. 1, 2009 (JP) ................................. 2009-274008
Jul. 23, 2010 (JP) ................................. 2010-166571

(51) Int. Cl.
| | | |
|---|---|---|
| *C12N 15/00* | (2006.01) | |
| *C12N 15/873* | (2010.01) | |
| *A01K 67/027* | (2006.01) | |
| *C12N 9/22* | (2006.01) | |
| *C12N 15/85* | (2006.01) | |
| *C12N 5/0735* | (2010.01) | |

(52) U.S. Cl.
CPC .......... *C12N 15/873* (2013.01); *A01K 67/0271* (2013.01); *A01K 67/0276* (2013.01); *C12N 9/22* (2013.01); *C12N 15/8509* (2013.01); *A01K 2217/00* (2013.01); *A01K 2217/052* (2013.01); *A01K 2227/105* (2013.01); *A01K 2267/0393* (2013.01); *C07K 2319/81* (2013.01); *C12N 5/0606* (2013.01); *C12N 15/85* (2013.01); *C12N 2500/30* (2013.01); *C12N 2501/065* (2013.01); *C12N 2501/15* (2013.01); *C12N 2501/998* (2013.01); *C12N 2501/999* (2013.01)

(58) Field of Classification Search
CPC ........... A01K 2217/00; A01K 2217/05; A01K 2217/07; A01K 2215/15; A01K 2227/10; A01K 2227/105; A01K 2267/03; A01K 2267/01; C12N 5/0606; C12N 5/0018; C12N 15/8509; C12N 15/873; C12N 15/8775; C12N 2501/15; C12N 2501/999; C12N 15/85; C12N 2500/30; C12N 2501/065; C12N 2501/998

See application file for complete search history.

(56) References Cited

U.S. PATENT DOCUMENTS

| | | |
|---|---|---|
| 6,103,523 A | 8/2000 | Moreadith et al. |
| 2005/0216966 A1 | 9/2005 | Nagao et al. |
| 2007/0186293 A1 | 8/2007 | Teratani et al. |
| 2010/0009442 A1 | 1/2010 | Sasai et al. |

FOREIGN PATENT DOCUMENTS

| | | |
|---|---|---|
| CN | 1217746 A | 5/1999 |
| CN | 1649489 A | 8/2005 |
| CN | 101563449 A | 10/2009 |
| JP | 2008-099662 A | 5/2008 |
| WO | WO 2005/085427 A1 | 9/2005 |
| WO | WO 2007/113505 A2 | 10/2007 |
| WO | WO 2008/015418 A2 | 2/2008 |

OTHER PUBLICATIONS

Li et al. Germline Competent Embryonic Stem Cells Derived from Rat Blastocysts. Cell, 2008, vol. 135, pp. 1299-1310 doi:10.1016/j.cell.2008.12.006.*
Li et al. Germline Competent Embryonic Stem Cells Derived from Rat Blastocysts. Cell, 2008, vol. 135, pp. 1299-1310.*
Buehr et al.Rapid Loss of Oct-4 and Pluripotency in Cultured Rodent Blastocysts and Derivative Cell Lines. Biology of Reproduction, 2003, vol. 68, pp. 222-229.*
Watanabe et al. A Rock inhibitor permits survival of dissociated human embryonic stem cells. Nature Biotechnology, 2007, vol. 25, pp. 681-686.*
Ogawa et al. Activin-Nodal signaling is involved in propagation of mouse embryonic stem cells. J. Cell Science, 2007, vol. 120, pp. 55-65.*
Buehr et al., *Cell*, 135(7): 1287-1298 (2008).
Hirabayashi et al., *Mol. Reprod. Dev.*, 77(2): 94 (2010).
Hirabayashi et al., *Mol. Reprod. Dev.*, 77(6): 474 (2010).
Kawamata et al., *PNAS*, 107(32): 14223-14228 (2010).
Li et al., *Cell*, 135(7): 1299-1310 (2008).
Li et al., *Cell Research*, 19(2): 173-186 (2009).

(Continued)

*Primary Examiner* — Deborah Crouch
(74) *Attorney, Agent, or Firm* — Leydig, Voit & Mayer, Ltd.

(57) ABSTRACT

The present invention provides a preparation method of a chimeric embryo and a chimeric rat, which is characterized by contacting a rat pluripotent stem cell and a host embryo in the presence of an ES cell differentiation inhibitor. The method includes (a) a step for contacting a fertilized host embryo collected from a female rat and a rat pluripotent stem cell in the presence of an ES cell differentiation suppressant, and (b) a step for culturing the host embryo in contact with the rat pluripotent stem cell to form a chimeric embryo.

13 Claims, 14 Drawing Sheets

(56) References Cited

OTHER PUBLICATIONS

Li et al., *Methods Mol. Biol.*, 636: 293-300 (2010).
Li et al., *Cell Stem Cell*, 4(1): 16-19 (2009).
Ueda et al., *PLoS One*, 3(7): e2800 (2008).
Chinese Patent Office, First Office Action in Chinese Patent Application No. 201080054625.6 (Apr. 1, 2013).
Japanese Patent Office, International Search Report in International Patent Application No. PCT/JP2010/071412 (Mar. 8, 2011).
The International Bureau of WIPO, International Preliminary Report on Patentability in International Patent Application No. PCT/JP2010/071412 (Jul. 10, 2012).
Kawamata et al., "Establishment of Embryonic Stem Cells from Rat Blastocysts," chapter 12 of "Rat Genomics: Methods and Protocols," *Methods in Molecular Biology*, 597: 169-177 (2010).
Liao et al., *Cell Stem Cell*, 4(1): 11-15 (2009).
Ying et al., *Nature*, 453(7194): 519-523 (2008).
European Patent Office, Extended European Patent Application No. 10834553.9 (Oct. 25, 2013).
Li et al., "Rat Embryonic Stem Cell Derivation and Propagation," chapter 19, pp. 457-475, in *Advanced Protocols for Animal Transgenesis*, Pease and Saunders (eds.), Springer Protocols Handbooks, Springer-Verlag Berlin Heidelberg (2011).

* cited by examiner (g)

(h)

(i)

FIG. 4-2
(i)
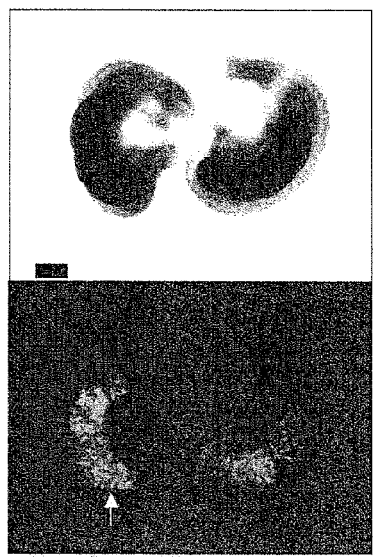
(j)
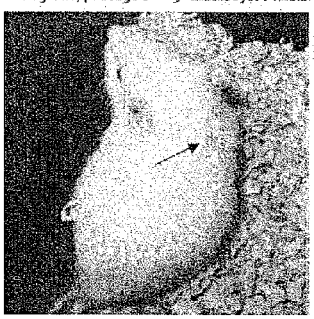
(k)

A

B P53-/- ES cell (p53^{C/R}) clone No.1, passage13

_US 9,309,537 B2_

CHIMERIC RAT PRODUCED USING RAT EMBRYONIC STEM CELLS IN THE PRESENCE OF AN ES CELL DIFFERENTIATION SUPPRESSANT

CROSS-REFERENCE TO RELATED APPLICATIONS

This patent application is the U.S. national phase of International Patent Application No. PCT/JP2010/071412, filed Nov. 30, 2010, which claims the benefit of Japanese Patent Application No. 2009-274008, filed Dec. 1, 2009, and Japanese Patent Application No. 2010-166571, filed on Jul. 23, 2010, which are incorporated by reference in their entireties herein.

TECHNICAL FIELD

The present invention relates to a method of preparing a chimeric embryo with improved germline transmission efficiency, which uses a rat pluripotent stem cell, particularly a rat embryonic stem cell (hereinafter to be referred to as "ES cell"), a method of preparing a chimeric rat by using the chimeric embryo, a chimeric rat prepared by the method, and a medium useful for preparing a chimeric rat.

BACKGROUND ART

ES cell is a nearly totipotent cell line and highly useful for the preparation of a genetically modified animal and the like. For example, a chimeric animal can be produced by injecting ES cells, in which a particular gene has been destructed, into normal host blastocysts to be mixed with the cells of the host embryos and returning the mixture to a uterus, and a genetically modified animal, in which the particular gene has been destructed (knockout animal), can be produced by crossing the obtained chimeric animals or offsprings and selecting the animals born.

Rat is a mammal having a size more suitable for handling than mouse, and is one of the most useful experimental animals widely utilized in various fields including medicine. Therefore, the establishment of rat ES cells and the production of chimeric rat using the cells have been desired. However, no technique has been established so far for efficiently preparing a chimeric rat wherein an ES cell differentiates into germ cell lineage and genetic information from the ES cell is transmitted to the next generation without being influenced by the strain of the rat ES cell and the strain of the host embryo (i.e., germline-transmitted chimeric rat).

Regarding the preparation of a chimeric rat with confirmed germline transmission, reports were presented by a group of Qi-Long Ying et al. and a group of Austin Smith et al., respectively, in 2008 (patent document 1, non-patent documents 1 and 2). In the two reports, chimeric rats were prepared using rat ES cells; however, in both cases, a germline-transmitted chimeric rat was successfully prepared from only one combination out of a plurality of combinations of ES cell strains and host embryo strains. It has been suggested that in the routinized practice of preparing a knockout rat, it is important to realize the preparation of a chimeric rat using a wide variety of combinations of ES cell strains and host embryo strains, which poses a problem to be solved in the future.

Also, despite the fact that some actual cases of generating a germline-transmitted chimeric rat have been reported, although they are limiting, as stated above, no report is available on the establishment of gene-targeted genetically modified rats (e.g., knockout rats, knockin rats). This may be due to an influence of the quality of the starting rat ES cell.

While rat iPS cell capable of producing chimeras is established using MEK inhibitor, GSK3 inhibitor and type I TGFβ receptor Alk5 inhibitor (A-83-01), germline transmission has not been achieved (non-patent document 3). In addition, it has also been reported that a combination of MEK inhibitor and Alk5 inhibitor strikingly improves efficiency of iPS cell production from human fibroblasts (non-patent document 4).

In recent years, Watanabe et al. have found that Rho-binding kinase (Rho-associated kinase; ROCK) inhibitor Y-27632 blocks apoptosis of human ES cell, and induces growth after single cell separation by an enzyme treatment (non-patent document 5), and also, usefulness of ROCK inhibitor for human stem cell culture has been reported (patent document 2).

DOCUMENT LIST

Patent Documents patent document 1: WO2008/015418
patent document 2: WO2008/035110

Non-Patent Documents non-patent document 1: Cell, 135, 1299-1310 (2008)
non-patent document 2: Cell, 135, 1287-1298 (2008)
non-patent document 3: Cell Stem Cell 4, 16-19 (2009)
non-patent document 4: Nat. Methods, 6, 805-808 (2009)
non-patent document 5: Mol. Pharmacol. 57, 976-983 (2000)

SUMMARY OF THE INVENTION

Problems to be Solved by the Invention

It is an object of the present invention to provide a method of preparing a novel chimeric embryo that makes it possible to efficiently obtain a germline-transmitted chimeric rat without limiting the combination of a rat pluripotent stem cell strain and a host embryo strain, a method of preparing a chimeric rat using the chimeric embryo, and a culture medium therefor, and to thereby provide a germline-transmitted chimeric rat comprising a combination of a rat pluripotent stem cell strain and a host embryo strain, which has conventionally been impossible to prepare.

It is another object of the present invention to provide a rat ES cell maintaining the capability of generating a chimeric rat, particularly the capability of transmitting a genetic modification to a germline, even after undergoing the genetic modification after preparation of the ES cell, and to provide a genetically modified, particularly gene-targeted genetically modified rat using the rat ES cell.

Means of Solving the Problems

The present inventors conducted extensive investigations to develop a method of preparing a chimeric rat using rat ES cells and, as a result, found that it was possible to efficiently prepare a chimeric embryo with improved germline transmission efficiency by injecting a rat ES cell into a host embryo in the presence of an ES cell differentiation suppressant, and that it was possible to prepare a germline-transmitted chimeric rat by using the chimeric embryo. It was found that when a small number of rat ES cells were injected into a host embryo, better results would be obtained in that the strength of adhesion of the ES cells to blastocysts would increase when the injection treatment was performed in the presence of an ROCK inhibitor in addition to an ES cell differentiation suppressant. Furthermore, the present inventors newly found that by using an ES cell differentiation suppressant, or by using the ES cell differentiation suppressant in combination with a ROCK inhibitor, it was possible to prepare a chimeric embryo with improved germline transmission efficiency using a wide variety of combinations of a rat ES cell strain and a host strain, and to efficiently prepare a germline-transmitted chimeric rat using the chimeric embryo.

Furthermore, the present inventors succeeded in establishing a rat ES cell maintaining the capability of generating a chimeric rat even after undergoing a genetic modification by adding an ES cell differentiation suppressant and a ROCK inhibitor to the medium when establishing the rat ES cell, and also succeeded in preparing a chimeric rat with a contribution of a gene-targeted ES cell using the ES cell.

The present inventors have conducted further studies based on these findings, which resulted in the completion of the present invention.

Accordingly, the present invention is as follows:
(1) A method of preparing a chimeric embryo, comprising the following steps (a) and (b):
(a) a step for contacting a fertilized host embryo collected from a female rat and a rat pluripotent stem cell in the presence of an ES cell differentiation suppressant,
(b) a step for culturing the host embryo in contact with the rat pluripotent stem cell to form a chimeric embryo.
(2) The method according to (1), wherein the contact is achieved by injecting the rat pluripotent stem cell into the host embryo.
(3) The method according to (1) or (2), wherein the rat pluripotent stem cell and the host embryo are contacted in the presence of the ES cell differentiation suppressant and a ROCK inhibitor in the step (a).
(4) The method according to any one of (1) to (3), wherein the rat pluripotent stem cell is a gene recombinant cell.
(5) The method according to any one of (1) to (4), wherein the host embryo is precultured in the presence of the ES cell differentiation suppressant before being contacted with the rat pluripotent stem cell.
(6) The method according to (5), wherein the preculture is performed in the presence of the ES cell differentiation suppressant and the ROCK inhibitor.
(7) The method according to any one of (1) to (6), wherein the cultivation in the step (b) is performed in the presence of the ES cell differentiation suppressant.
(8) The method according to (7), wherein the cultivation in the step (b) is performed in the presence of the ES cell differentiation suppressant and the ROCK inhibitor.
(9) The method according to any one of (1) to (8), wherein the ES cell differentiation suppressant consists of at least 2 kinds of drugs selected from the group consisting of an MEK inhibitor, a GSK3 inhibitor, a TGFβ receptor inhibitor, and an FGF receptor inhibitor.
(10) The method according to (9), wherein the ES cell differentiation suppressant consists of an MEK inhibitor, a GSK3 inhibitor, and a TGFβ receptor inhibitor.
(11) The method according to any one of (1) to (10), wherein the pluripotent stem cell is an ES cell.
(12) The method according to any one of (1) to (11), wherein the rat pluripotent stem cell is a pluripotent stem cell prepared from a rat of a strain that does not produce a germline-transmitted chimeric rat when contacted with a host embryo in the absence of an ES cell differentiation suppressant in the step (a).
(13) The method according to any one of (1) to (12), wherein the host embryo is derived from a rat of a strain that does not produce a germline-transmitted chimeric rat when contacted with a rat pluripotent stem cell in the absence of an ES cell differentiation suppressant in the step (a).
(14) A method of preparing a chimeric rat, comprising transplanting a chimeric embryo prepared by the method according to any one of (1) to (13) to the uterus or oviduct of a pseudopregnant female rat to allow an offspring rat to be born.
(15) The method according to (14), further comprising confirming germline transmission in the chimeric rat.
(16) A germline-transmitted chimeric rat obtained by transplanting a chimeric embryo prepared by the method according to (12) or (13) to the uterus or oviduct of a pseudopregnant female rat to allow an offspring rat to be born.
(17) A method of preparing a rat with a contribution of a rat pluripotent stem cell to the whole body, comprising mating a chimeric rat having germline transmission confirmed by the method according to (15) with a rat of the opposite sex.
(18) A culture medium for preparing a chimeric rat, comprising an MEK inhibitor, a GSK3 inhibitor, and a TGFβ inhibitor.
(19) The culture medium according to (18), further comprising a ROCK inhibitor.
(20) A use of an ES cell differentiation suppressant for producing a culture medium for preparing a chimeric rat.
(21) A use of an ES cell differentiation suppressant and a ROCK inhibitor for producing a culture medium for preparing a chimeric rat.
(22) The use according to (20) or (21), wherein the ES cell differentiation suppressant is an MEK inhibitor, a GSK3 inhibitor, and a TGFβ inhibitor.
(23) A germline transmission efficiency improving agent for chimeric rats, comprising an ES cell differentiation suppressant.
(24) The agent according to (23), further comprising a ROCK inhibitor.
(25) The agent according to (23) or (24), wherein the ES cell differentiation suppressant consists of at least 2 kinds of drugs selected from the group consisting of an MEK inhibitor, a GSK3 inhibitor, a TGFβ receptor inhibitor, and an FGF receptor inhibitor.
(26) The agent according to (25), wherein the ES cell differentiation suppressant consists of an MEK inhibitor, a GSK3 inhibitor, and a TGFβ receptor inhibitor.
(27) A method of preparing an ES cell using an ES cell differentiation suppressant and a ROCK inhibitor.
(28) The method according to (27), wherein the ES cell differentiation suppressant consists of a combination of an MEK inhibitor, a GSK3 inhibitor, and a TGFβ receptor inhibitor, or a combination of an MEK inhibitor, a GSK3 inhibitor, and a FGF receptor inhibitor.
(29) A method of preparing an ES cell using the culture medium according to (19).
(30) The method according to any one of (27) to (29), wherein the ES cell is a rat ES cell capable of maintaining the capability of generating a chimeric rat even after undergoing a genetic modification.
(31) The method according to (30), wherein the genetic modification is a modification by gene targeting.
(32) The method according to (30) or (31), wherein the chimeric rat is a germline-transmitted chimeric rat.
(33) A rat ES cell capable of maintaining the capability of generating a chimeric rat even after undergoing a genetic modification.

(34) The method according to (33), wherein the genetic modification is a modification by gene targeting.
(35) The cell according to (33) or (34), wherein the chimeric rat is a germline-transmitted chimeric rat.
(36) A genetically modified chimeric rat with a contribution of the genetically modified rat ES cell according to any one of (33) to (35).
(37) The rat according to (36) with a contribution of the genetically modified ES cell to a germ cell line.
(38) A rat with a contribution of a genetically modified ES cell to the whole body, obtained by mating the rat according to (37).
(39) A culture medium for preparing a rat ES cell capable of maintaining the capability of generating a chimeric rat even after undergoing a genetic modification, comprising an ES cell differentiation suppressant and a ROCK inhibitor.
(40) A culture medium for preparing a rat ES cell capable of maintaining the capability of generating a chimeric rat even after undergoing a genetic modification, comprising an MEK inhibitor, a GSK3 inhibitor, a TGFβ receptor inhibitor, and a ROCK inhibitor.
(41) A genetically modified rat with a contribution of a rat ES cell undergoing a biallelic genetic modification.
(42) A method of preparing a genetically modified rat, comprising a step for performing a biallelic genetic modification on a rat ES cell.

Effect of the Invention

According to the present invention, irrespective of the strain of the rat pluripotent stem cell or the strain of the host embryo, a chimeric embryo with improved germline transmission efficiency can be prepared; by using the chimeric embryo, a germline-transmitted chimeric rat can be prepared at high efficiency. Thereby it is possible to easily prepare a genetically modified rat (knockout rats, knockin rats, and the like) that can be widely used for a wide variety of pharmacological studies or physiological studies, as well as for regenerative medicine studies and the like.

BRIEF DESCRIPTION OF THE DRAWINGS

FIG. 2-1 A drawing showing the results of an examination of the characteristics of rat ES cells. (a) shows photographs of colonies showing influences of Y-27632. Separated single cells ($1 \times 10^5$ TgWW1 cells, number of passages 6) were seeded to a 6-well plate. The left panel shows colonies obtained with addition of MEF+YPAC factors to the culture medium, the central panel shows colonies obtained with addition of PAC factor, and the right panel shows colonies obtained with addition of Y factor. (b) shows photographs of alkaline phosphatase (ALP) staining of the same various cells. (c) is a photograph of Giemsa staining of 50 cells of TgWL2 (number of passages: 7). TgWL2 (number of passages: 7) exhibited the karyotype of 42 chromosomes including the XX sex chromosome. (d) is a graphic representation comparing gene expression patterns by scatter plot analysis. TgWW1 and REF are shown in the left panel, and TgWW1 and LL are shown in the right panel. An Agilent gene chip (whole rat genome microarray kit) was used for microarray analysis. The center line represents the equivalence curve; the lines above and below it show that the sample gene expression levels differed 2 fold. (e) is a graphic representation comparing the gene expression patterns for REF, TgWL1, TgWW1, and LL. These are the results of Q-PCR of Venus, Oct4, Nanog, Sox2, and Rex1 in rat ES cell lines. The data are means for three independent experiments, being relative gene expression levels in REF, TgWL1, TgWW1, and LL. (f) is a photograph showing a teratoma formation from rat cells. This is a teratoma generated by subcutaneously transplanting $2.6 \times 10^6$ TgWW1 (number of passages: 5) cells to an immunodeficient mouse.

FIG. 2-2 (g) is a drawing showing the results of microarray analysis and hierarchical cluster analysis. A one-color microarray based gene expression analysis containing 41,000 genes (Agilent Technology) was used. The numerical values on the panel indicate correlation coefficients. (h) shows immunostaining charts of Oct4, Nanog, and Sox2 in rat ES cells (lower panels). The upper panels show DAPI staining images. (i) shows cross-sectional views of the three germ layers of teratoma induced from the TgWW1 ES cell line.

FIG. 4-1 A graphic representation concerning the preparation of germline chimeras by the YPAC injection method. (a) is a drawing showing the expression of AmCyan1 in stably transformed clones by introduction of p-CAG-AmCyan1 plasmid into nucleic acids. (b) shows photographs of the results of an examination of the influences of the YPAC factors in the injection process. The images obtained with addition of the YPAC factors to the ES basal medium are shown in the right panels, and those obtained without addition are shown in the left panels. The upper panels are photographs taken 5 hours after incubation; the lower panels are photographs taken 30 hours after incubation. (c) shows photographs of fetal germline chimeras. TgWW1+C cells were injected into Wistar blastocysts. Venus and AmCyan1 fluorescence was detected in the whole fetus, kidney, and testis at 18 days. (d) shows the genesis of chimeric color rats by the YPAC injection method. (e) shows germline transmission in an adult chimera. The chimera (TgWL1) was mated with a female Wistar. Germline individuals (4/16) were identified by their coat color. (f) shows a genotyping analysis of F1 of female chimera (TgWL2). The Venus region, after collecting tail genomic DNA, was amplified by PCR. Three out of six individuals were identified as germline individuals. The Venus gene had a 199 bp size; M indicates a 100 bp DNA marker. Lanes 1, 2, and 3 show germline individuals with agouti coat color, and lanes 4, 5, and 6 show individuals negative for agouti coat color (albino). (g) shows photographs of single cells (TgWW1) injected into blastocysts. The blastocysts were photographed at 3 hours of incubation after the injection. Each arrow indicates an injected cell. (h) shows photographs of chimeric rat fetuses with confirmed germline transmission. Venus-positive germ cells were detected on one side of the gonad at 16 days. The scale bar is 100 μm.

FIG. 4-2 (i) shows germline transmission in long-subcultured ES cells. Long cultured ES cells (TgWL2: number of passages: 22) were injected into blastocysts; 17.5 days later, Venus fluorescence on the gonad was detected (scale bar: 300 μm). The upper panel shows a bright field image, and the lower panel shows a fluorescence image. (j) shows an example of a coat color chimera obtained by injection without addition of the YPAC factors. (k) shows an example of a coat color chimera obtained by injection with addition of YPAC.

DESCRIPTION OF EMBODIMENTS

Figure 1:
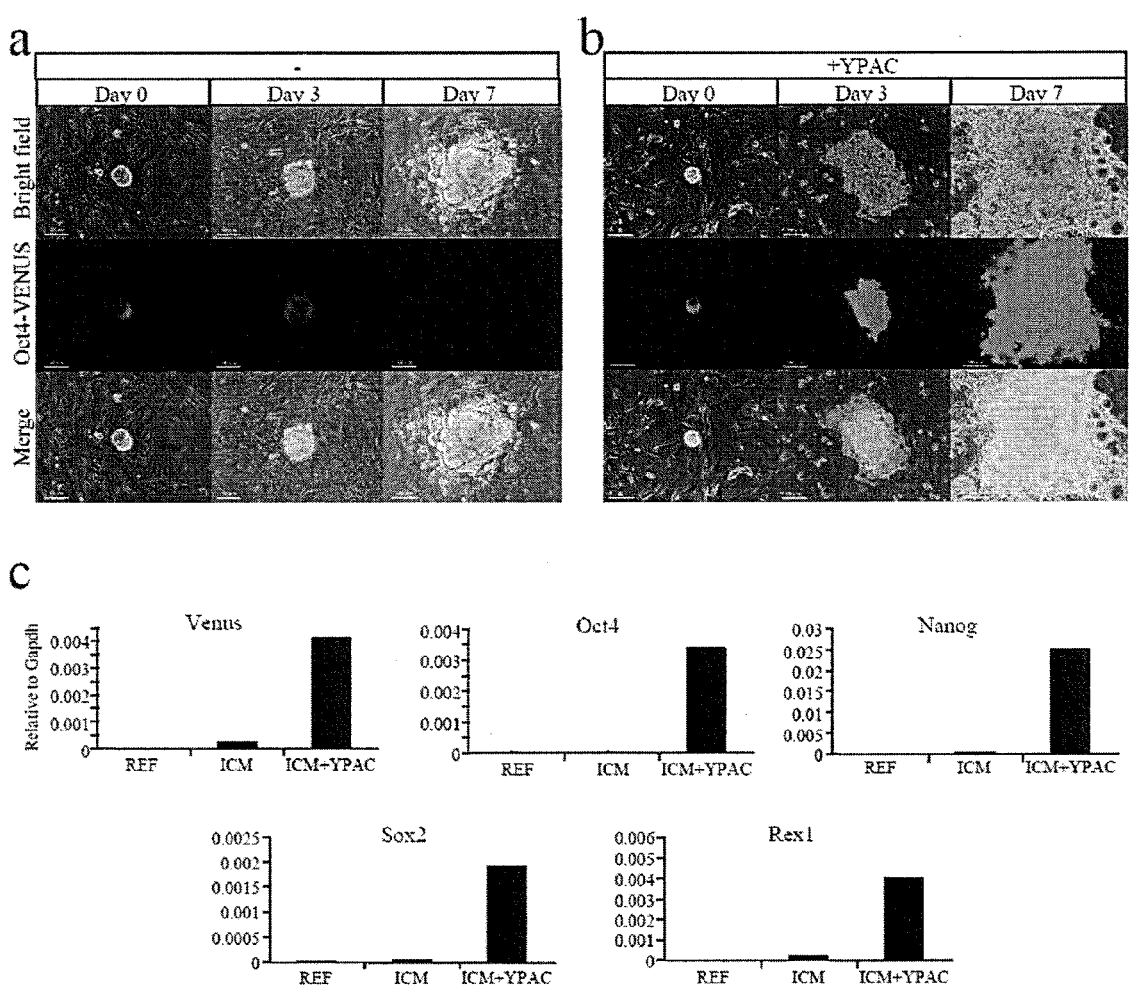
FIG. 1 shows photographs of outgrowths of blastocysts in an ES cell culture medium (a) without addition of the YPAC factors, and (b) with addition of the YPAC factors. Blastocysts at 4.5 days were seeded onto division-inactivated MEF. The zona pellucida was removed using the Tyrode buffer solution. (c) is a graphic representation showing the results of quantitative PCR analyses of Venus, Oct4, Nanog, Sox2, and Rex1 in inner cell mass (ICM). Seven days after seeding, RNA was extracted from the dome-like portion in the ICM induced from 7 or 4 blastocysts without addition of the YPAC factors and with addition of the YPAC factors. The data are means for three independent experiments, being relative gene expression levels in REF, ICM, and ICM+YPAC factors.

The present invention provides a method of efficiently preparing a germline-transmitted chimeric rat using a rat pluripotent stem cell without being subject to limitations to a particular strain of a rat pluripotent stem cell or a strain of a host embryo. Described below are a rat pluripotent stem cell according to the present invention, a method of preparing a chimeric embryo and a chimeric rat, a method of preparing a genetically modified rat, and a kit for preparing a chimeric rat.

1. Rat Pluripotent Stem Cell

In the present invention, "a pluripotent stem cell" refers to a cell that maintains undifferentiated state and pluripotency, represented by ES cells and induced pluripotent stem cells (iPS cells). The ES cell may be an ES cell resulting from nuclear reprogramming of a somatic cell but is preferably prepared from rat early embryo by the method described later. Besides ES cells, examples include embryonic germ cells (EG cells) derived from primordial germ cells, multipotent germline stem cells (mGS cells) isolated from the testis, and the like. Preferably, the rat pluripotent stem cell to be used in the present invention is rat ES cell or rat iPS cell, more preferably rat ES cell.

1-1. Rat ES Cell

A rat ES cell used for the production of a chimeric rat in the present invention may be derived from any strain of rat, as long as it can produce a germline transmitted chimeric rat. While the strain of the rat is not particularly limited, for example, it is selected from the rat strains such as Wistar Kyoto strain (WKY), Brown Norway strain (BN), Goto-Kakizaki strain (GK), SD strain, F344/Du strain (Fischer), Wistar strain, Wistar Hannover strain, Long-Evans Agouti strain (LEA), ACI strain and the like. Also, in the present invention, the strain may be a pure strain or a strain obtained by hybridizing 2 strains or more. Taking into account the feature of the present invention that a germline-transmitted chimeric rat can be efficiently prepared irrespective of the strain of the rat ES cell, the present invention is particularly useful in using an ES cell prepared from a rat strain that does not produce a germline-transmitted chimeric rat when the rat ES cell is contacted with a host embryo in the absence of an ES cell differentiation suppressant in the step described below for contacting the host embryo and the rat ES cell.

Rat ES cells capable of producing a germline transmitted chimeric rat can be obtained for the cell lines exemplified above from given institutions, or can also be produced according to a method known per se. Examples of the production method of the rat ES cell include the method of Buehr M et al. (Cell 2008; 135:1287-1298) and the like.

Rat ES cell having an ability to prepare a germline transmitted chimeric rat can also be established and prepared by performing a process comprising the following steps (A)-(C):
(A) a step for dissociating an inner cell mass formed by the culture of rat blastocysts, (B) a step for culturing primary embryonic stem cells resulting from the culture of the dissociated inner cell mass until it can be passaged, (C) a step for dissociating the primary embryonic stem cells, which have become capable of being passaged, remaining a state of cell aggregate, and culturing the same.

The cultivation in the above-described method of preparation is performed preferably using a medium containing at least 2 kinds of ES cell differentiation suppressants, more preferably using a medium containing at least 2 kinds of ES cell differentiation suppressants and a ROCK inhibitor. Here, "an ES cell differentiation suppressant" means a substance, other than leukemia inhibitory factor (LIF), that is capable of suppressing the differentiation of ES cells into other cells or tissues and the like, and, in the present invention, may be any substance that possesses the action of suppressing the differentiation of rat ES cells. ES cell differentiation suppressants include, for example, MEK inhibitors, GSK3 inhibitors, TGFβ receptor inhibitors, FGF receptor inhibitors and the like. For this cultivation, specifically, it is preferable to use a medium containing an MEK inhibitor and a GSK3 inhibitor; it is more preferable to use a medium containing an MEK inhibitor, a GSK3 inhibitor, an FGF receptor inhibitor, and a ROCK inhibitor; it is still more preferable to use a medium containing an MEK inhibitor, a GSK3 inhibitor, a TGFβ receptor inhibitor, and a ROCK inhibitor; it is particularly preferable to use a medium containing an MEK inhibitor, a GSK3 inhibitor, a TGFβ receptor inhibitor, and a ROCK inhibitor.

By using a medium containing an ES cell differentiation suppressant and a ROCK inhibitor, it is possible to prepare a rat ES cell capable of maintaining the capability of generating a chimeric rat, particularly the capability of generating a germline-transmitted chimeric rat, even after undergoing to a genetic modification after establishment of the ES cell.

MEK inhibitor is not particularly limited as long as it has an action to inhibit the function of MEK (MAP kinase-ERK kinase) and, for example, AZD6244, CI-1040 (PD184352), PD0325901, RDEA119 (BAY869766), SL327, U0126 (all the above, Selleck), PD98059, U0124, U0125 (all the above, COSMO BIO Co., Ltd.) and the like can be mentioned. The concentration of the MEK inhibitor to be added to a medium can be appropriately selected from the range of, for example, 0.01-100 μm, preferably 0.1-5 μM.

GSK3 inhibitor is not particularly limited as long as it has an action to inhibit the function of glycogen synthase kinase (GSK) 3 and, for example, SB216763 (Selleck), CHIR98014, CHIR99021 (all the above, Axon Medchem), SB415286 (Tocris Bioscience), Kenpaullone (COSMO BIO Co., Ltd.) and the like can be mentioned. The concentration of the GSK3 inhibitor to be added to a medium can be appropriately selected from the range of, for example, 0.01-100 μm, preferably 1-10 μm.

TGFβ receptor inhibitor is not particularly limited as long as it has an action to inhibit the function of transforming growth factor (TGF)β receptor and, for example, 2-(5-benzo[1,3]dioxol-4-yl-2-tert-butyl-1H-imidazol-4-yl)-6-methylpyridine, 3-(6-methylpyridin-2-yl)-4-(4-quinolyl)-1-phenylthiocarbamoyl-1H-pyrazole (A-83-01), 2-(5-chloro-2-fluorophenyl)pteridin-4-yl)pyridin-4-ylamine (SD-208), 3-(pyridin-2-yl)-4-(4-quinonyl)]-1H-pyrazole, 2-(3-(6-methylpyridin-2-yl)-1H-pyrazol-4-yl)-1,5-naphthyridine (all the above, Merck), SB431542 (Sigma Aldrich) and the like can be mentioned. The TGFβ receptor inhibitor also includes TGFβ receptor antagonists. The concentration of the TGFβ receptor inhibitor to be added to a medium can be appropriately selected from the range of, for example, 0.01-10 μm, preferably 0.1-1 μM.

FGF receptor inhibitor is not particularly limited as long as it has an action to inhibit the function of fibroblast growth factor (FGF) receptor and, for example, SU5402 (COSMO BIO Co., Ltd.), PD173074 (STEMGENT) and the like can be mentioned. The FGF receptor inhibitor also includes FGF receptor antagonists. The concentration of the FGF receptor inhibitor to be added to a medium can be appropriately selected from the range of, for example, 0.005-500 μm, preferably 0.07-50 μm.

ROCK inhibitor is not particularly limited as long as it has an action to inhibit the function of Rho-binding kinase. Examples of the ROCK inhibitor include GSK269962A (Axon Medchem), Fasudil hydrochloride (Tocris Bioscience), Y-27632, H-1152 (all the above, Wako Pure Chemical Industries, Ltd.) and the like. The concentration of the ROCK inhibitor to be added to a medium can be appropriately selected from the range of, for example, 0.0001-500 μm, preferably 1-50 μm.

The basal medium to be used for establishment and culture of rat ES cell is not particularly limited as long as it can be used for culturing animal cells. Examples thereof include BME medium, BGJb medium, CMRL 1066 medium, Glasgow MEM medium, Improved MEM Zinc Option medium, IMDM medium, Medium 199 medium, Eagle MEM medium, aMEM medium, DMEM medium, hamF12 medium, RPMI 1640 medium, Fischer's medium, and mixed medium thereof and the like.

The culture medium may be a serum-containing culture medium or a serum-free culture medium. When using an unconditioned or unpurified serum, the serum must be added to the culture medium to the extent that does not make the rat ES cells to lose their capability of generating a germline-transmitted chimeric rat due to an influence of the serum. When adding a serum at 5% or more, for example, at about 10 to about 20%, it is desirable that a serum conditioned or purified for ES cell culture be used. Such sera for ES cell culture (for example, bovine fetal serum) are commercially available.

The medium can also contain fatty acid or lipid, amino acid (e.g., non-essential amino acid), vitamin, growth factor, cytokine, antioxidant, 2-mercaptoethanol, pyruvic acid, buffering agent, inorganic salts and the like.

In the cultivation of rat ES cells, a leukemia inhibitory factor (LIF) can also be used. The LIF is particularly preferably rat-derived LIF (rLIF). The LIF can be used as added to the culture medium as appropriate in the cultivation in the step (B) and step (C) in the above-described method of preparation. Meanwhile, in the step (A), to increase inner cell mass formation efficiency, rat ES cell establishment efficiency, and rat ES cell quality, it is rather preferable that the concentration of rLIF for addition to the culture medium be not more than 100 units per mL of the culture medium, and it is more preferable that the rat ES cells be cultured using an LIF-free culture medium at least until the inner cell mass formation stage, preferably over the entire step (A). For rLIF, commercial products (Chemicon Company and the like) may be purchased and utilized.

It is preferable to further use feeder cells for the production and culture of rat ES cells. Feeder cells may be ones derived from any species available to one of ordinary skill in the art, and are preferably normal fibroblasts rather than established lines of feeder cells. Specifically, normal mouse embryonic fibroblasts can be mentioned. More specifically, primary cultured cells of mouse embryonic fibroblasts (normal fibroblasts) between the 12th and 16th days of pregnancy can be mentioned. As the normal fibroblasts, for example, normal fibroblasts of ICR fetal mouse at the 12.5th day are exemplified. The feeder cells can be prepared by a conventional method. Commercially available products (mouse fibroblasts; Asahi Techno Glass Corporation, etc.) can be also utilized. It is preferable to use the feeder cells inactivated by the treatment with mitomycin C and the like.

The culture vessel used to culture rat ES cells is not particularly limited, as far as it is for cell culture; such culture vessels include, for example, flasks, tissue culture flasks, dishes, Petri dishes, tissue culture dishes, multi-dishes, microplates, micro-well plates, multi-plates, multi-well plates, chamber slides, Petri dishes, tubes, trays, culturing bags, roller bottles, and the like. The culture vessel may be non-cell-adhesive or cell-adhesive. A cell-adhesive culture vessel whose surface is coated with a cell support substratum for the purpose of improving adhesion with the cells can be used; such cell support substrata include, for example, collagen, gelatin, Matrigel, poly-L-lysine, laminin, fibronectin and the like.

The cultivation can be performed, for example, in a $CO_2$ incubator under an atmosphere of about 1-about 10%, preferably about 2-about 5%, more preferably about 5%, $CO_2$ concentration, at about 30-about 40° C., preferably about 35-about 37.5° C., more preferably about 37° C.

As other components in the medium, components conventionally used for the culture of ES cells are appropriately contained by combining them within the common knowledge of one of ordinary skill in the art.

A specific composition of the medium is exemplified in the following.

1) Medium (Culture Medium) for Rat ES Cell Establishment

A culture medium used in the steps from blastocysts to inner cell mass formation is referred to as "culture medium for rat ES cell establishment".

(Specific Example of Composition)

DMEM Including 110 mg/L Sodium Pyruvate and 200 mM GlutaMax (GIBCO)
20% FBS (ES Cell Qualified FBS) (GIBCO)
0.1 mM 2-Mercaptoethanol (Sigma)
1% Non Essential Amino Acid Stock (GIBCO)
1% ixAntibiotic antimycotic (GIBCO)
10 µM Y-27632 (WAKO)
1 µM PD0325901 (Axon Medchem)
0.5 µM A-83-01 (TOCRIS)
3 µM CHIR99021 (Axon Medchem)

2) Medium (Culture Medium) for Rat ES Cells

A culture medium used in the culture after inner cell mass formation (including culture of established rat ES cells) is referred to as "culture medium for rat ES cells".

(Specific Example of Composition)

The culture medium for ES cells is similar to that for the production of rat ES cell, and may further contain a rat leukemia inhibitory factor (rLIF). rLIF is preferably added and mixed just before use.

(1) Method for Rat ES Cell Establishment

A specific example of the method for establishing rat ES cell of the present invention is shown in the following.

1) Oocyte (Embryo in Blastocyst Stage) Sampling

As a rat for oocyte sampling, a rat from the strains such as the aforementioned Wistar Kyoto (WKY) strain, Brown Norway (BN) strain, Goto-Kakizaki (GK) strain, SD strain, F344/Du (Fischer) strain, Wistar strain, Wistar Hannover strain, Long-Evans Agouti strain (LEA) and ACI strain can be used.

A rat within the range of 8 to 40 weeks old can be used, preferably a 10 to 20-week-old rat is used, more preferably a 10 to 12-week-old rat is used.

Oocyte sampling may be carried out by a conventional method known to one of ordinary skill in the art. Specifically, rats are naturally crossed, the female rat for oocyte sampling is sacrificed to excise an uterus about 4-5 days after vaginal plug detection. This uterus is perfused with a suitable medium to recover fertilized oocytes (embryos). The culture medium used herein includes, for example, mw medium (640.0 mg/100 ml NaCl, 35.6 mg/100 ml KCl, 16.2 mg/100 ml $KH_2PO_4$, 29.4 mg/100 ml $MgSO_4$-$7H_2O$, 190.0 mg/100 ml $NaHCO_3$, 100.0 mg/100 ml glucose, 2.5 mg/100 ml Na-pyruvate, 46.0 mg/100 ml Ca-lactate, 5.0 mg/100 ml streptomycin, 7.5 mg/100 ml penicillin, 0.5% phenrol red (0.2 ml), 20 mM beta-ME (10 µl), 100 mM EDTA-2Na (10 µl), 300.0 mg/100 ml BSA), M2 medium (0.251 g/L calcium chloride-$2H_2O$, 0.143 g/L magnesium sulfate, 0.356 g/L potassium chloride, 0.162 g/L potassium phosphate, 5.532 g/L sodium chloride, 4.0 g/L albumin, 1.0 g/L D-glucose, 4.969 g/L HEPES, 0.01 g/L phenol red-Na, 0.036 g/L pyruvic acid-Na, 0.35 g/L sodium bicarbonate, 0.06 g/L penicillin G, 0.05 g/L streptomycin sulfate, 4.349 g/L D,L-lactic acid) and the like.

The recovered embryos can also be cultured in a culture medium such as mw medium, M2, M16, and the like. By this culture, the development proceeds from fertilized oocytes (embryos) through moluras to blastocysts (embryos in blastocyst stage). To promote the development to this stage, the culture is typically performed in a 5% $CO_2$ incubator at 37° C. overnight. It can be confirmed by microscopic observations that the development has proceeded to blastocyst stage. Preferably, the development proceeds up to the late blastocyst stage.

2) Formation and Separation of Inner Cell Masses

The blastocysts obtained in the aforementioned 1) are confirmed microscopically, and zona pellucidas are removed. The zona pellucidas is removed using Acidic Tyrode (pH 2.5), hyaluronidase, pronase and the like. Then, feeder cells treated with mitomycin C are sown onto culture dishes, zona pellucida-removed rat blastocysts are transferred to the dishes, and the culture is started using a culture medium for rat ES cell establishment.

Between the 1st and 4th days of the culture, zona pellucida-removed rat blastocysts (late stage) adhere to the feeder cells. On 5-10 days after adhesion, an inner cell mass appeared from the blastocysts is mechanically separated using a 200 µl pipette and the like. This separated inner cell mass is mechanically dissociated using a pipette or a protease such as trypsin-EDTA, Accutase (registered trade mark, Innovative Cell Technologies) and the like. This dissociation step is preferably carried out by using a pipette and the like until the mass becomes cell aggregates consisting of about 5-20 cells. The maintained state of cell aggregates can be confirmed microscopically.

3) Establishment of ES Cells

In the gelatin-coated culture dishes wherein the feeder cells are sown, inner cell masses dissociated in the aforementioned 2) are cultured in a culture medium for rat ES cells. Primary ES cell colony usually appears between the 2nd and 4th days from the start of the culture. The appearance of the primary ES cell colony can be confirmed by microscopic observations (the appeared ES cells are referred to as "primary ES cells"). By continuing the culture about 5-10 days thereafter, the primary ES cell colony becomes in a state capable of being passaged. The "state capable of being passaged" used herein means a state wherein the number of cells constituting the primary ES cell colony formed has reached approximately 200-600, and each cellular interval has become tight and the cell mass shows a dome-like form with gloss. While microscopically confirming that it has such morphology, the ES cell colony is separated using a 200 µl of pipette and the like. This separated ES cell colony is transferred to a sterilized tube and the like containing a culture medium for rat ES cells, and mechanically dissociated until it becomes cell aggregates consisting of about 5-20 cells, or by using a protease such as Accutase (registered trade mark). A mechanical dissociation is preferable. The dissociated ES cell colony is subjected to a primary culture (cells at passage 1) in a culture medium for rat ES cells in a gelatin-coated culture dish wherein the feeder cells are sown. An ES cell colony appears about 2-4 days after the start of the culture and becomes in a state capable of being passaged in about 5-10 days.

After removing the culture medium, the ES cell colony that has become capable of passaged in the above and the entire surface thereof is coated with Accutase (registered trade mark) or 2.5% trypsin previously incubated at 37° C. When microscopically confirming a state of 70% or more of the whole ES cell colony coming unstuck from the feeder cells, the protease treatment is immediately stopped. The protease treatment can be stopped by, for example, adding a culture medium containing 10% fetal bovine serum or a large amount of a serum-free culture medium. Then, the ES cell colony is further unstuck mechanically using a 5 ml of pipette and the like, the cell suspension is centrifuged (for about 3 minutes at room temperature, 1000 rpm) to separate the cells and the culture medium and only the cells are recovered. The cells are suspended in a culture medium for rat ES cells, after microscopically confirming a state that the cells form aggregates of 5-20 cells rather than becoming fully single cells, the cells are transferred to culture dishes wherein the feeder cells are sown and cultured (cells at passage 2).

After that, since the cells become in a state capable of passaged every about 3-5 days, they can be continuously passaged and cultured by dissociating the cells with a protease such as Accutase (registered trade mark) or mechanically dissociating the cells.

It can be confirmed that the rat ES cell retains a property for an ES cell, that is, the desirable property for an ES cell maintaining the undifferentiated state (totipotency) by, for example, examining the expression of an ES cell-specific gene (for example, Oct3/4 gene, Nanog gene), alkaline phosphatase activity, embryoid body formation capacity, the expression of SSEA-1 and SSEA-4, the number of chromosomes, the condition after subculture, in vitro multipotency, the capability of differentiation into cells of the three germ cells, teratoma formation capability and the like. Verifications thereof can be achieved using techniques known per se (see, for example, WO 2005/085427), and some specific examples are given in Examples below.

1-2. Rat iPS Cells

Rat iPS cells can be prepared according to, for example, the method described in Cell Stem Cell 4, 16-19 (2009). As the starting material rat somatic cells, fetal, infantile, or adult somatic cells collected from the aforementioned strains of rat ES cells can be used. Specifically, tissue stem cells (somatic stem cells) such as nerve stem cells, hematopoietic stem cells, mesenchymal stem cells, sperm stem cells and the like; tissue progenitor cells; already differentiated cells such as lymphocytes, epithelial cells, muscle cells, fibroblasts and the like; and the like can be used. As the reprogramming factor used for nuclear reprogramming, in addition to those used in the aforementioned references, reprogramming factors that can be used to establish iPS cells in mouse, human, and other mammals can also be selected and used as appropriate, to the extent possible. As the MEK inhibitor, GSK3 inhibitor, and TGFβ inhibitor used to improve nuclear reprogramming efficiency, the same substances as those mentioned above with respect to the establishment of rat ES cells can be selected and used as appropriate. Maintenance of the undifferentiated state (totipotency) by the established rat iPS cells can be confirmed by the method described above.

2. Methods of Preparing a Chimeric Embryo and a Chimeric Rat

The present invention provides a method of preparing a chimeric embryo with improved germline transmission efficiency, and a method of preparing a chimeric rat by obtaining an offspring rat from a rat undergoing transplantation of the chimeric embryo. By using the methods of the present invention, it is possible to efficiently provide a germline-transmitted chimeric rat without being limited by the strain of the rat pluripotent stem cell or host embryo.

Rat is a mammal having an experimentally suitable size of about 10 times the size of mouse, and is advantageous in that (1) drug administration into the blood vessel in the cell is easy, (2) a surgical or transplantation test can be performed, (3) a large amount of tissue can be collected and the like. While many human disease model rats have been conventionally developed and discovered, since a method of preparing a germline-transmitted chimeric rat efficiently without being limited to rat ES cell strains and host rat strains was not established, preparation of a genetically modified rat, particularly a genetically modified rat requiring gene targeting such as knockout rat and knockin rat, has not been performed.

Using a chimeric rat prepared by the method of the present invention, a genetically modified rat can be produced easily, without limitation by rat pluripotent stem cell lineage and host rat lineage. Here, the "genetically modified rat" means any genetically modified rat known to those of ordinary skill in the art, such as chimeric rat, knockout rat, knockin rat, transgenic rat and knockdown rat.

More specifically, the preparation method of a chimeric embryo of the present invention includes the following steps (a) and (b):

(a) a step for contacting a fertilized host embryo collected from a female rat and a rat pluripotent stem cell in the presence of an ES cell differentiation suppressant, (b) a step for culturing the host embryo in contact with the rat pluripotent stem cell to form a chimeric embryo.

In addition, the preparation method of a chimeric rat of the present invention includes a step for transplanting a chimeric embryo prepared by the above method to the uterus or oviduct of a pseudopregnant female rat to allow an offspring rat to be born.

The rat pluripotent stem cell used to prepare a chimeric rat in the present invention is a cell mentioned in "1. Rat pluripotent stem cells" above, preferably a rat ES cell or a rat iPS cell, more preferably a rat ES cell. The rat pluripotent stem cell may be a gene recombinant cell having a particular gene recombined by a publicly known method. Examples include ES cells artificially deprived of a particular gene, ES cells artificially incorporating a particular gene, and the like.

A rat from which a host embryo in the present invention is obtained may be derived from any strain of rat. For example, the rat strain includes Wistar Kyoto strain (WKY), Brown Norway strain (BN), Goto-Kakizaki strain (GK), SD strain, F344/Du strain (Fischer), Wistar strain, Wistar Hannover strain, Long-Evans Agouti strain (LEA), ACI strain and the like. In the present invention, the strain may be a pure strain or a strain obtained by hybridizing 2 kinds or more. Taking into account the feature of the present invention that a germline-transmitted chimeric rat can be efficiently prepared irrespective of the strain of the rat ES cell, the present invention is particularly useful in using a host embryo collected from a rat strain that does not produce a germline-transmitted chimeric rat when the rat ES cell is contacted with a rat pluripotent stem cell in the absence of an ES cell differentiation suppressant in the step for contacting the host embryo and rat pluripotent stem cell.

A female rat for oocyte sampling within the range of 8 to 40 weeks old can be used, preferably a 10 to 20-week-old rat is used, more preferably a 10 to 12-week-old rat is used.

The starting material host embryo is not particularly limited, as far as it is a fertilized early embryo collected from a female rat; usually, early embryos prior to the blastocyst stage (for example, 8-cell stage embryos, 16-cell stage embryos, morula stage embryos, blastocyst stage embryos) and the like may be mentioned.

A host embryo can be collected from a mated female rat by a method known per se. The mating may be spontaneous mating, or may be performed after induction of ovulation. The method of collecting the host embryo is not particularly limited; to explain specifically, a female rat for egg collection is mated with a male rat of the same strain spontaneously or after administration of gonadotropic hormones (follicle-stimulating hormone, then luteinizing hormone) to induce overovulation, after which the female rat for egg collection is killed, the uterus is extirpated, at an appropriate time (for example, 3.5 days after mating for 8-cell stage embryos, 3.75 days after mating for 16-cell stage embryos, 4 days after mating for morula stage embryos, 4.5 days after mating for blastocyst stage embryos), and the uterus is perfused with an appropriate culture medium, whereby an early embryo can be recovered. Here, examples of the culture broth used for perfusion include the above-described culture broths for establishing rat ES cells, the above-described mw culture medium that is also used for recovering the early embryo, M2 culture medium and the like.

The collected host embryo can be cultivated before contact with a rat pluripotent stem cell. As a basal medium for the preculture, one similar to the basal medium used for establishing the rat ES cell can be used. The medium can be a serum-containing medium or serum-free medium. The medium can also contain fatty acid or lipid, amino acid (e.g., non-essential amino acid), vitamin, growth factor, cytokine, antioxidant, 2-mercaptoethanol, pyruvic acid, buffering agent, inorganic salts and the like.

In a preferable embodiment, an ES cell differentiation inhibitor is added to the above-mentioned preculture medium. As the ES cell differentiation inhibitor, at least two kinds of drugs selected from MEK inhibitor, GSK inhibitor, TGFβ receptor inhibitor, and FGF receptor inhibitor can be mentioned. As the MEK inhibitor, GSK inhibitor, TGFβ receptor inhibitor and FGF receptor inhibitor, the substances mentioned above for the culture of rat ES cell can be used. The ES cell differentiation inhibitor is preferably a combination including an MEK inhibitor and a GSK inhibitor, and a more preferable example is a combination further using a TGFβ receptor inhibitor.

The concentration of the MEK inhibitor to be added to a medium can be appropriately selected from the range of, for example, 0.01-100 μm, preferably 0.1-5 μM. The concentration of the GSK3 inhibitor to be added to a medium can be appropriately selected from the range of, for example, 0.01-100 μm, preferably 1-10 μm. The concentration of the TGFβ receptor inhibitor to be added to a medium can be appropriately selected from the range of, for example, 0.001-10 μm, preferably 0.1-1 μM. The concentration of the FGF receptor inhibitor to be added to a medium can be appropriately selected from the range of, for example, 0.005-500 μm, preferably 0.07-50 μm.

In another preferable embodiment, a ROCK inhibitor can be further added to a medium for host embryo preculture, in addition to an ES cell differentiation inhibitor. Specific examples of the ROCK inhibitor include the substances mentioned above for rat ES cell culture. The concentration of the ROCK inhibitor to be added to a medium can be appropriately selected from the range of, for example, 0.0001-500 μm, preferably 1-50 μm.

The preculture can be performed, for example, in a $CO_2$ incubator under an atmosphere of about 1-about 10%, preferably about 2-about 5%, more preferably about 5%, $CO_2$ concentration, at about 30-about 40° C., preferably about 35-about 37.5° C., more preferably about 37° C.

The rat pluripotent stem cell to be contacted with the host embryo is selected as appropriate from among those described in 1 above, and is preferably the rat ES cell described in 1-1 above. For facilitating the preparation of a chimeric rat, it is desirable that the rat pluripotent stem cell be a recombinant rat pluripotent stem cell having a reporter gene (for example, GFPs (including modified GFPs such as EGFP and Venus), β-gal, luciferase and the like) introduced thereinto in advance by a conventional method. In the selection of a chimeric rat using a coat color only, germline transmission will be confirmed in an offspring generation; however, provided that a reporter pluripotent stem cell is used, germline transmission can be confirmed in the present generation of the chimeric rat by detecting the expression of the reporter in the germ cells of the chimeric rat. Specifically, a transgenic rat incorporating the reporter gene may be prepared in advance, and a pluripotent stem cell may be obtained from the rat as described above; alternatively, an expression vector containing a transformant cell selection marker gene such as a drug resistance gene, along with the reporter gene, may be introduced into a rat pluripotent stem cell prepared as described above by electroporation and the like, and a rat ES cell incorporating the reporter gene may be selected by drug selection and the like.

Rat pluripotent stem cell can be contacted with a host embryo by a method known to the artisan. For example, rat pluripotent stem cell is transplanted into a blastocoele of a rat blastocyst or into morula stage or 16-cell stage embryo by a microscopic manipulation and developed with an inner cell mass or as a part of an inner cell mass (microinjection method: Gordon J. W. et al., Proc. Natl. Acad. Sci. USA., 77: 7380-7384 (1980)). Alternatively, zona pellucidas are removed from two 8-cell embryos and pluripotent stem cell is injected and the embryos are co-cultured to form an aggregate. When the resulting aggregate is cultivated, one blastocyst is obtained (cell aggregate method: Dvorak P. et al., Int. J. Dev. Biol., 39: 645-652 (1995)). When rat pluripotent stem cell is injected, rat ES cell is preferably covered with mineral oil, oil drop, liquid paraffin etc. and the injection into the host embryo is performed.

As a medium used for contacting a rat pluripotent stem cell and a host embryo, one similar to the basal medium used for establishing the rat ES cell can be used as a basal medium. The medium can be a serum-containing medium or serum-free medium. The medium can also contain fatty acid or lipid, amino acid (e.g., non-essential amino acid), vitamin, growth factor, cytokine, antioxidant, 2-mercaptoethanol, pyruvic acid, buffering agent, inorganic salts and the like.

Two or more kinds of ES cell differentiation inhibitors are added to the contact medium. The at least two kinds of the ES cell differentiation inhibitors are selected from MEK inhibitor, GSK inhibitor, TGFβ receptor inhibitor, and FGF receptor inhibitor. Examples of the MEK inhibitor, GSK inhibitor, TGFβ receptor inhibitor and FGF receptor inhibitor include the substances mentioned above for the culture of rat ES cell. The at least two kinds of ES cell differentiation inhibitors preferably include a combination including an MEK inhibitor and a GSK inhibitor, and a more preferable example is a combination further using a TGFβ receptor inhibitor.

The concentration of the MEK inhibitor to be added to a medium can be appropriately selected from the range of, for example, 0.01-100 μm, preferably 0.1-5 μM. The concentration of the GSK3 inhibitor to be added to a medium can be appropriately selected from the range of, for example, 0.01-100 μm, preferably 1-10 μm. The concentration of the TGFβ receptor inhibitor to be added to a medium can be appropriately selected from the range of, for example, 0.001-10 μm, preferably 0.1-1 μM. The concentration of the FGF receptor inhibitor to be added to a medium can be appropriately selected from the range of, for example, 0.005-500 μm, preferably 0.07-50 μm.

In a preferable embodiment, a ROCK inhibitor can be further added to the contact medium, in addition to an ES cell differentiation inhibitor. Specific examples of the ROCK inhibitor include the substances mentioned above for rat ES cell culture. The concentration of the ROCK inhibitor to be added to a medium can be appropriately selected from the range of, for example, 0.0001-500 μm, preferably 1-50 μm.

After being contacted with the rat pluripotent stem cell, the host embryo can form a chimeric embryo when continued to be cultured. This culture medium for after-cultivation may be of the same composition as the aforementioned culture medium for contacting; the culture medium is preferably one containing an ES cell differentiation suppressant, more preferably a culture medium containing 2 kinds or more of ES cell differentiation suppressants. Specifically, a culture medium containing an MEK inhibitor and a GSK3 inhibitor is preferable, and a culture medium containing an MEK inhibitor, a GSK3 inhibitor, and a TGFβ receptor inhibitor is more preferable. Furthermore, a ROCK inhibitor may be added to the culture medium.

The post-culture can be performed under the conditions similar to those for the aforementioned preculture.

The chimeric embryo prepared above is transplanted in the uterus or oviduct of a pseudopregnant female rat prepared by natural crossbreeding with a male rat after vasoligation treatment to make the rat produce offspring rats, whereby a chimeric rat can be obtained.

The fact that the chimeric rat prepared by the method of the present invention has a tissue derived from a rat pluripotent stem cell can be confirmed by, for example, the expression of a coat color of the rat strain from which the rat pluripotent stem cell is derived, the expression of a reporter gene in a tissue section of the chimeric rat in the chimeric rat, and the like. In particular, by detecting differentiation into a germ cell line by the expression of a reporter gene in the germ cells, it is possible to confirm the presence or absence of germline transmission quickly and conveniently. Final confirmation of germline transmission can be achieved by, for example, extracting DNA from cells of an offspring rat obtained by sibling mating of the chimeric rats, and detecting the presence of the reporter gene by Southern blotting, genome PCR and the like.

By mating a chimeric rat with confirmed germline transmission with a rat of the opposite sex, it is possible to prepare a rat having rat pluripotent stem cells contributing to the whole body thereof, i.e., a rat all of whose cells carry genetic information derived from rat pluripotent stem cells. For example, the offspring rat obtained by mating a germline-transmitted chimeric rat and a wild type rat will have only one of the homologous chromosomes thereof derived from rat pluripotent stem cells, whereas the offspring rat obtained by sibling mating of the chimeric rats will have both of the homologous chromosomes derived from rat pluripotent stem cells.

3. Method of Preparing a Genetically Modified Rat

As stated above, by mating a germline-transmitted chimeric rat with a rat of the opposite sex, it is possible to prepare a rat having rat pluripotent stem cells contributing to the whole body thereof; therefore, by genetically modifying the rat pluripotent stem cells, it is possible to create a genetically modified rat all of whose cells have the genetic modification. Accordingly, the present invention also provides a method of preparing a genetically modified rat using a chimeric rat prepared by "2. Methods of preparing a chimeric embryo and a chimeric rat" above, and a genetically modified rat prepared by the method. Here, the "genetically modified rat" means any genetically modified rat known to those of ordinary skill in the art, such as knockout rat, knockin rat, transgenic rat and knockdown rat.

Preferably, the chimeric rat used to prepare a genetically modified rat is a chimeric rat having rat ES cells established using an ES cell differentiation suppressant and a ROCK inhibitor, described in 1-1 above, contributing thereto.

Knockout rat means a mutant rat wherein a target gene has been artificially destroyed, and is also called a gene targeting rat. A knockout rat can be prepared, for example, according to a preparation method of a knockout mouse as described in Donehower, A. L. et al. *Nature*, 356: 215-221 (1992) and the like. To be specific, a vector for homologous recombination (targeting vector) is constructed based on the genomic DNA sequence of a target gene. At this time, a drug resistant gene such as a G418 resistant gene, a hygromycin resistant gene and the like is incorporated as a marker gene for selection of a recombinant clone. The constructed targeting vector is introduced into the rat pluripotent stem cell by an electroporation method and the like. From the obtained cells incorporating the targeting vector, a colony in which a homologous gene recombination has occurred is selected based on the marker gene etc. Using the thus-obtained gene recombinant rat pluripotent stem cell, a chimeric rat is produced according to the chimeric rat production method of the present invention. By crossing the chimeric rat with a wild-type rat, a heterozygous knockout rat can be produced in the offspring rats thereof, and when heterozygous knockout rats are crossed, a homozygous knockout rat can be produced in the offspring rats thereof.

In recent years, it has been possible to easily perform a biallelic modification of a target gene at the cell level. Specifically, for example, this can be facilitated by using a technique such as zinc finger nuclease (ZFN). Therefore, for rat ES cells, a homo-knockout rat can easily be produced by causing the target gene to undergo a biallelic deficiency using these publicly known techniques, and using the biallelically deficient ES cell.

The category of the aforementioned knockout rat includes a conditional knockout rat. The conditional knockout means a system to site-specifically or time-specifically knockout a gene utilizing a Cre/loxP system or a FLP/FRT system. To be specific, the both ends (3'-terminal and 5'-terminal) of a gene to be targeted is substituted by a gene flanked by loxP sequences or FRT sequences, and Cre or FLP protein is supplied to cleave the gene flanked by the aforementioned loxP sequences or FRT sequences (Sternberg N., et al., *J. Mol. Biol.*, 150: 487-507 (1981)).

Knockin rat means a mutant rat in which an artificially prepared exogenous gene having homology to a target gene has been introduced into the site thereof. The function of a target gene may or may not be destroyed by the introduction of the exogenous gene. For example, to monitor expression of the target gene, a marker gene such as a lacZ gene, a GFP gene and the like may be introduced or a gene may be exchanged to one in which a mutation has been introduced.

The knockin rat can be produced, for example, according to a preparation method of a knockin mouse as described in Pewzner-Jung, Y. et al., *J. Immunol.*, 161: 4634-4645 (1998) and the like. Basically, the rat can be produced by the same principle as in the aforementioned knockout rat.

The "transgenic rat" means a rat in which a foreign gene has been artificially introduced. A transgenic animal is conventionally prepared by injection of a desired gene by microscopic manipulation into the male pronucleus of a fertilized oocyte collected from a donor animal (microinjection method). The fertilized egg is transplanted into the oviduct of the recipient animal, and the naturally born animal becomes a transgenic animal. The need for the chimeric rat is not as high as in the case of the aforementioned knockout rat and knockin rat. However, the preparation method of chimeric rat of the present invention is effectively used for increasing the introduction efficiency of an exogenous gene and preparation efficiency of an individual transgenic animal.

The transgenic rat can be produced, for example, according to the preparation method of transgenic mouse as described in Yamamoto H. et al., *Cancer Res.*, 62: 1641-1647 (2002) and the like.

The category of the aforementioned transgenic rat includes a conditional transgenic rat. The conditional transgenic means a system to site-specifically or time-specifically express a gene utilizing a Cre/loxP system or a FLP/FRT system. To be specific, expression of an object gene is inhibited by inserting, into the object gene, a cassette wherein the both ends (3'-terminal and 5'-terminal) of a drug resistant gene etc. is flanked by loxP sequences or FRT sequences, and Cre or FLP protein is supplied to cleave the gene flanked by the loxP sequences or FRT sequences, whereby the object gene is expressed (Sternberg, N., et al., *J. Biol.*, 150: 487-507 (1981)).

Knockdown rat means a rat, into which a short double strand RNA (siRNA), which is an intermediate for RNAi (RNA interference), or antisense nucleic acid has been artificially introduced and expressed, and expression of the target gene is suppressed by the action of the siRNA or antisense nucleic acid. Preparation of such knockdown animal has been enabled based on the establishment of an expression system of siRNA by a vector system (*Science* 296: 550-553 (2002), *Nature Biotech*. 20: 500-505 (2002) etc.).

The knockdown rat can be produced, for example, according to the method described in Tiscornia, G. et al., *Proc. Natl. Acad. Sci. USA*. 100: 1844-1848 (2003) and the like. Basically, the rat can be produced by the same principle as in the aforementioned transgenic rat.

4. Kit for Preparing a Chimeric Rat

The present invention provides a kit comprising a culture medium for preparing a germline-transmitted chimeric rat. The culture medium (for example, culture broth) contained in the kit of the present invention can also be used to establish a rat ES cell possessing the capability of generating a germline-transmitted chimeric rat.

It is a feature of the kit of the present invention that it comprises a culture medium containing an ES cell differentiation suppressant as a component. The ES cell differentiation suppressant may be any substance, as far as it possesses the action of suppressing the differentiation capability of rat ES cells in the present invention. ES cell differentiation suppressants include, for example, MEK inhibitors, GSK3 inhibitors, TGFβ receptor inhibitors, and FGF receptor inhibitors. Of these, in the present invention, at least 2 kinds of ES cell differentiation suppressants are used. Preferably, ES cell differentiation suppressants include the combination of an MEK inhibitor and a GSK inhibitor, the combination of an MEK inhibitor, a GSK inhibitor, and a TGFβ receptor inhibitor, and the combination of an MEK inhibitor, a GSK inhibitor, and an FGF receptor inhibitor; because of the high capability of generating a germline-transmitted chimeric rat, MEK inhibitors, GSK3 inhibitors, and TGFβ receptor inhibitors are more preferable. In another preferred mode of embodiment, in addition to an ES cell differentiation suppressant, a ROCK inhibitor may be further added. Details of MEK inhibitors, GSK3 inhibitors, TGFβ receptor inhibitors, FGF receptor inhibitors, and ROCK inhibitors are as described above.

The kit of the present invention can contain the aforementioned ES cell differentiation suppressants alone or in combination of at least 2 kinds or more as appropriate. When 2 kinds or more of ES cell differentiation suppressants are contained in combination in the kit, the various ES cell differentiation suppressants may be mixed and enclosed in one container, but they are preferably enclosed in separate containers.

The kit can comprise a rat pluripotent stem cell as defined in "1. Rat pluripotent stem cells" above as a kit component. The rat pluripotent stem cell is preferably a rat ES cell.

The aforementioned kit can further contain a feeder cell as a constituent component. The feeder cell may be one derived from any species available to one of ordinary skill in the art, and is preferably normal fibroblast rather than an established line of feeder cell. Specifically, primary cultured cells of mouse embryonic fibroblasts (normal fibroblasts) between the 12th and 16th days of pregnancy can be mentioned. As the normal fibroblasts, for example, normal fibroblasts of ICR fetal mouse at the 12.5th day are exemplified. The feeder cells can be prepared by a conventional method. Commercially available mouse embryonic fibroblasts (Asahi Techno Glass Corporation), etc. can also be utilized.

EXAMPLES

The Examples of the present invention are explained in the following, which are not to be construed as limitative.

Example 1

Preparation of Fluorescence Reporter Transgenic Rats

To establish and verify ES cells, a transgenic rat was prepared for monitoring the expression of the Oct4 gene by fluorescence. The Oct4 promoter region DNA was amplified from Wistar rat genomic DNA by a PCR using KOD Ver. 2 DNA polymerase (Toyobo), and inserted into the pCS2-Venus plasmid. The Oct4 promoter-Venus DNA was injected into the pronucleus of a fertilized egg of a Wistar rat to obtain an Oct4-VENUS transgenic rat.

Example 2

Preparation of Rat ES Cells (1) Preparation of Reagents and Feeder Cells

First, 4 kinds of inhibitors, i.e., Y-27632, a ROCK inhibitor (WAKO Company), PD0325901, an MEK inhibitor (Axon Medchem Company), A-83-01, a type I TGF-β receptor inhibitor (TOCRIS Company), and CHIR99021, a GSK3 inhibitor (Axon Medchem Company), were prepared (hereinafter, these 4 kinds of inhibitors are referred to as "the YPAC factors").

The basal medium for ES cells was prepared by adding 20% FBS for ES cells (Lot No. 1204059: GIBCO Company), 0.1 mM 2-Mercaptoethanol (Sigma Company), 1% Non Essential Amino Acid Stock (GIBCO Company), and 1% 1×Antibiotic antimycotic (GIBCO Company) to a DMEM (GIBCO Company) containing 110 mg/L Sodium Pyruvate and 200 mM GlutaMax.

The YPAC factors were added to this basal medium for ES cells to obtain concentrations of 10 μM for the ROCK inhibitor Y-27632, 10 μM for the MEK inhibitor PD0325901, 0.5 μM for the type I TGF-β receptor inhibitor A-83-01, and 3 μM for the GSK3 inhibitor CHIR99021, and the medium was used for the experiments (hereinafter, this medium is referred to as "the YPAC culture medium").

The feeder cells used were mitomycin C treated neomycin-resistant mouse embryonic fibroblasts (MEF: Millipore), which were maintained using a culture medium prepared by adding 10% FBS (EQUITECH-BIO Company, Lot No. SFB30-1502) and 1% 1×Antibiotic antimycotic (GIBCO Company) to DMEM.

(2) Establishment of ES Cells

Rat blastocysts were obtained by perfusing the uterus of a pregnant rat at 4.5 or 5 days of gestation with the basal medium for ES cells. After removing the zona pellucida using the Tyrode buffer solution (Ark Resource Company), the blastocysts were transferred to a 6-well plate and cultured using the basal medium for ES cells prepared by adding the YPAC factors in (1) to feeder cells (MEF) (the YPAC culture medium). About 7 days later, outgrowths of the blastocysts were reseeded to the YPAC culture medium; ES cell colonies were enzymatically separated using Accutase (Innovative cell technologies Company) and cultured. The established ES cells were cultured under MEF-YPAC culture medium conditions and passaged every 3 to 4 days. The ES cells were frozen and thawed according to a conventional method with addition of DMSO (dimethylsulfoxide) to the YPAC culture medium. TgWL1 (ES cells) and TgWL2 (ES cells) were cultured with addition of 1000 U/mL rLIF until the number of passages reached 3 or 4.

(3) Investigation Using a Wide Variety of Strains of Rats

Using the method of establishing rat ES cells described in (2) above, an investigation was performed to determine whether rat ES cells could be established for non-Wistar strains of rats. As a result, rat ES cells were able to be established for all strains investigated, as shown in Table 1.

TABLE 1

| Strain | No. ICMs | Outgrowth[b] | Continue | Cell line[c] |
|---|---|---|---|---|
| TgWL | 2 | 2 | 2 | 2 |
| TgWW | 15 | 15 | 1 | 1 |
| WW | 9 | 9 | 1 | 1 |
| LL | 19 | 19 | 2 | 2 |
| TgWW[a] | 3 | 3 | 2 | 2 |
| WW[a] | 3 | 3 | 0 | 0 |
| Total | 51 | 51 (100%) | 8 | 8 (100%) |

[a]Different media were used (FBS: MEF culture, EQUITECH + BIO)
[b]Outgrowth indicates an elongation of ICM.
[c]Cell Line indicates that cultivation continued at least by a number of passages of 7. Single cell subculture was started between numbers of generations 1 and 2. Dome colonies of undifferentiated cells were continuously formed from single cells.
TgWL: Transgenic hybrid between Wistar and LEA
TgWW: Transgenic hybrid between Wistar and wild type Wistar
WW: Wild type Wistar
LL: LEA Example 3

Verification of Rat ES Cells

Verification was performed for the rat ES cells obtained in Example 2 and the process of their preparation.
(1) Outgrowths of Inner Cell Masses (ICMs) in the YPAC Culture Medium Using inner cell masses (ICMs) from blastocysts of the transgenic rat prepared in Example 1, an investigation was performed with and without addition of the YPAC factors to the basal medium for ES cells of Example 2. In the absence of the YPAC factors, Oct4-Venus fluorescence was detected 3 days after plate seeding; 7 days later; however, a dome-like growth similar to a mouse ES colony appeared but then disappeared. In the presence of the YPAC factors, the ICM cells grew rapidly while maintaining the Oct4-Venus fluorescence even 7 days later (FIGS. 1a and b). The gene expression of the pluripotency factors Oct4, Nanog, Sox2, and Rex1 was examined by quantitative PCR; higher levels were found with addition of the YPAC factors than in the absence of the YPAC factors. In the absence of the YPAC factors, the Oct4 mRNA decreased like the expression of Venus mRNA and fluorescence intensity (FIG. 1c). In this experiment, the blastocysts used were those derived from transgenic Wistar (TgWW, Arbino), Wild-type Wistar (WW, albion), LEA (LL, agouti), or a transgenic Wistar/LEA (TgWL, agouti) hybrid. The rat ES cells established in the presence of the YPAC factors were confirmed to express Oct4, Nanog, and Sox2 even by immunostaining (FIG. 2h).

(2) Verification of the Effects of Y Factor (ROCK Inhibitor) in Culture Medium

Figures 1, 2:
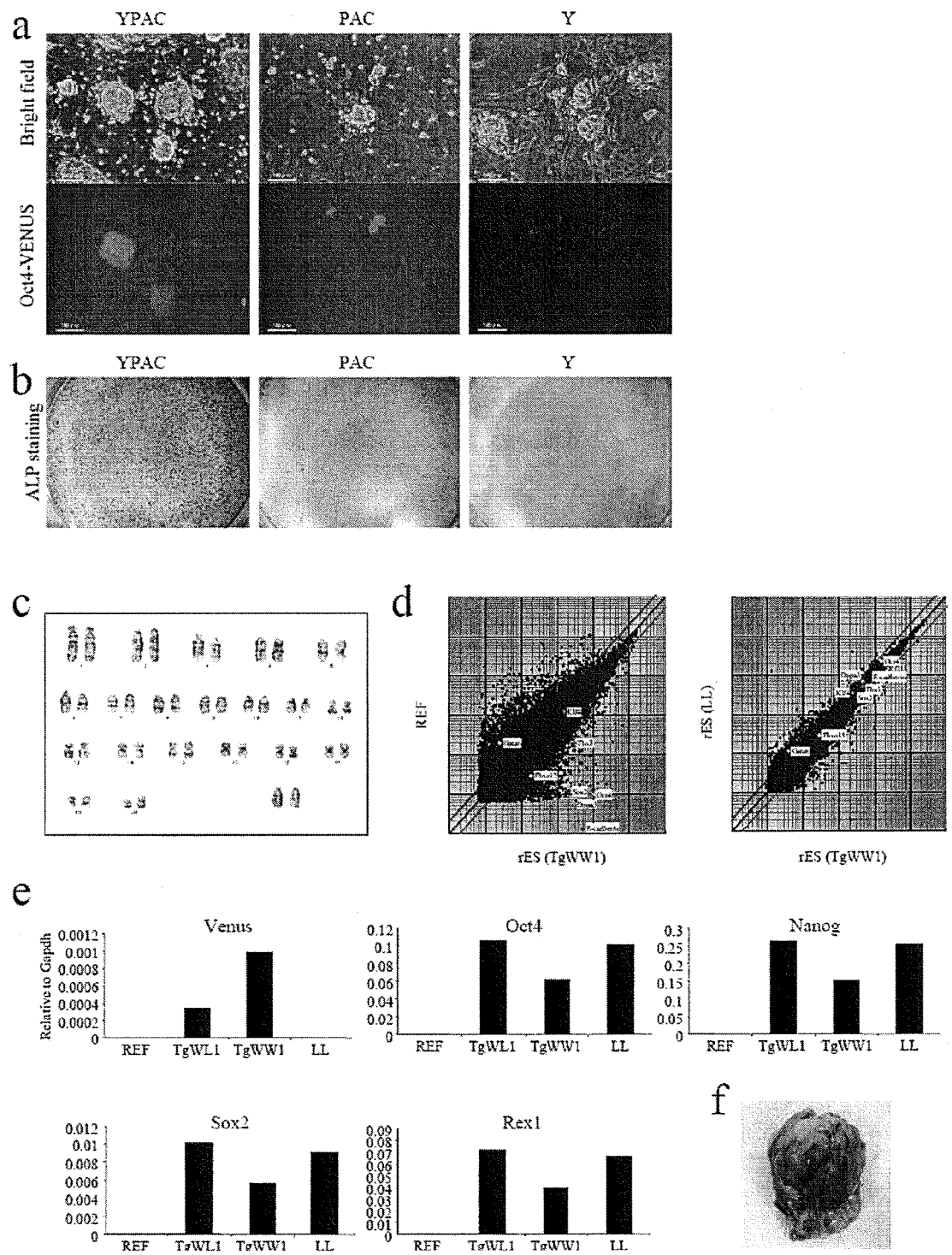
Figure 2:
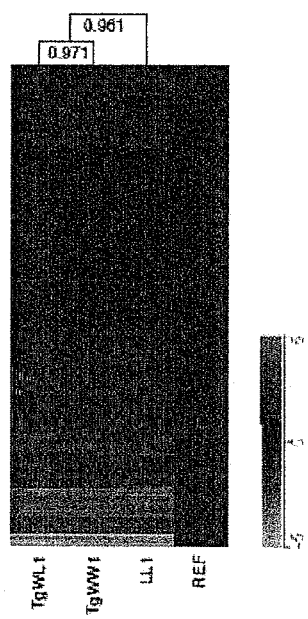
Figure 2:
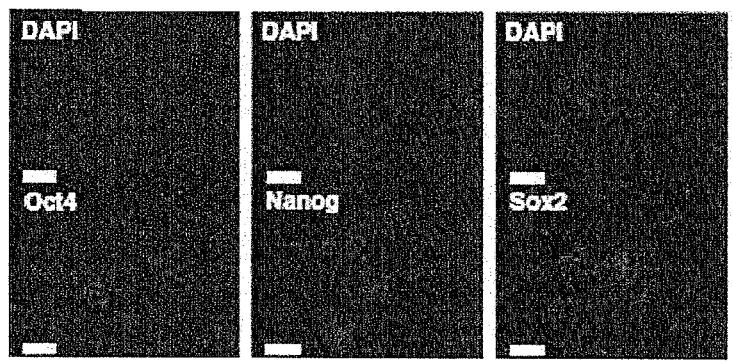
Figure 2:
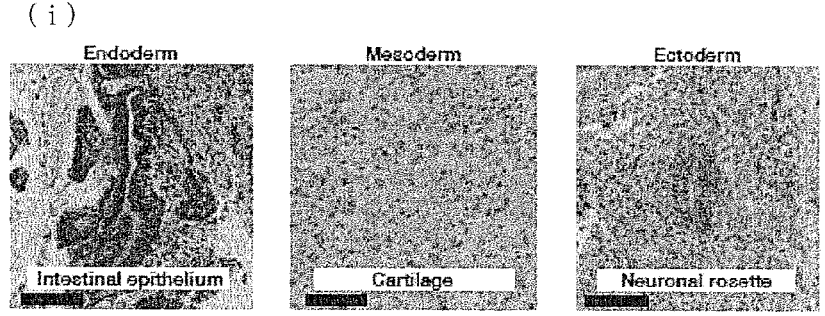

When the established rat ES cells were cultured using an ES cell culture medium not containing a ROCK inhibitor (hereinafter, referred to as "the Y factor"), but supplemented with an MEK inhibitor, a type I TGF-β receptor inhibitor, and a GSK3 inhibitor (hereinafter, these 3 kinds of inhibitors are referred to as "the PAC factor"), the resulting colonies maintained the undifferentiated state but became sparse colonies (FIG. 2a). Meanwhile, when cultured using an ES cell culture medium supplemented with the Y factor alone, the rat ES cells adhered onto MEF and proliferated, but were unable to maintain the undifferentiation state and did not exhibit alkaline phosphatase activity (FIGS. 2a, b).

(3) Karyotype Analysis in ES Cells

The 50 rat ES cells obtained were analyzed for karyotype by Giemsa staining; almost all of the cells exhibited the normal 42-chromosome karyotype (FIG. 2c). The results were TgWL1 (70%, XX, P14), TgWL2 (84%, XX, P7, FIG. 2c), TgWW1 (92%, XX, P5), and LL1 (84%, XX, P6).

(4) DNA Microarray Analyses
(i) Microarray Analysis 1

As a result of microarray analysis, the TgWW1 and LL ES cells were found to be similar in gene expression, but a difference was noted between TgWW1 and rat embryonic fibroblasts (REFs). Statistical analysis on ES cells revealed a correlation coefficient of 0.968; although the expression levels of the pluripotency markers Oct4, Sox2, Dppa3, Tbx3, Fbxo15, and Cdh1, also known as E-cadherin, were similar in TgWW1 and LL (FIG. 2d), but higher than in REF (FIG. 2e).

(ii) Microarray Analysis 2

As a result of microarray analysis, the TgWL1, TgWW1, and LL1 ES cells were found to be similar in gene expression, but a difference was noted between ES cells and rat embryonic fibroblasts (REFs) (FIG. 2g). Statistical analysis on ES cells revealed a correlation coefficient of 0.971 between TgWL1 and TgWW1 and 0.961 between TgWW1 and LL1.

(5) Formation of Teratomas

The TgWW1 cells (ES cells) prepared in Example 2 were dispersed into single cells using Accutase, after which the cells were twice washed with 10 mL of PBS, and $2.6 \times 10^6$ cells in suspension in 100 μL of PBS were subcutaneously injected into an immunodeficient mouse; a teratoma was detected in the mouse at 34 days (FIG. 2f). The teratoma was fixed in paraffin wax and subjected to histological staining using hematoxylin-eosin; differentiation into the three germ layers of the endoderm, mesoderm, and ectoderm was confirmed (FIG. 2i).

(6) Formation of ES Cell Embryoid Bodies (Embryoid Bodies: EBs)

Figure 3:
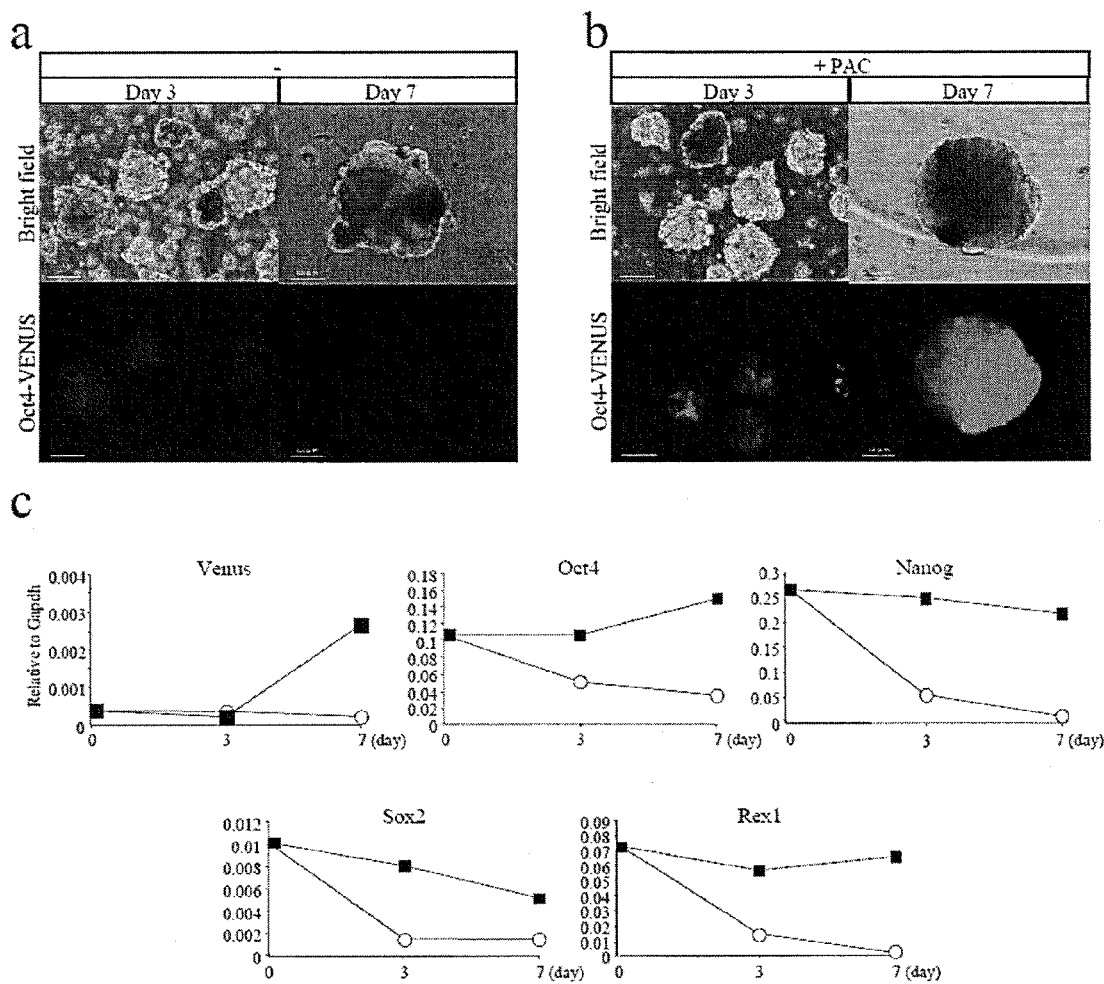
FIG. 3 is a graphic representation showing the results of an examination of the effects of embryo bodies (EBs) and the YPAC factors. Shown are photographs of embryo bodies (TgWL1) taken 3 days and 7 days after cultivation in the absence of Y-27632 in a basal medium for ES cells (a) without addition of PAC factor and (b) with addition of PAC factor. (c) is a graphic representation showing the results of Q-PCR analyses of Venus, Oct4, Nanog, Sox2, and Rex1 in EBs. The data are means for three independent experiments, being gene expression levels in ES cells at 0, 3, and 7 days of cultivation without addition of an inhibitor (outlined circles) and with addition of PAC factor (solid squares).

The rat ES cells prepared in Example 2 were dispersed into single cells using Accutase, after which the cells were cultured using an ES cell culture medium prepared by adding 3 inhibitors (PAC factors), excluding the Y factor, to the ES cell culture medium of Example 2 on a low-adhesion dish (NUNC Company) to yield embryoids (EBs); the cells aggregated at high efficiency, forming clear three-dimensional EBs (FIG. 3b). Oct4-Venus fluorescence intensity increased at 7 days, and it was confirmed by quantitative PCR that the expression of Venus, Oct4, Nanog, Sox2, and Rex1 was also maintained (FIG. 3c). Meanwhile, without addition of the PAC factors, the efficiency of preparation of EBs was remarkably lower than with mouse EBs (FIG. 3a), but the expression of the various pluripotency marker genes decreased (FIG. 3c).

Example 4

Preparation of Germline Transmission Chimeric Rats by YPAC Injection Using Multiple Strains Germline transmission chimeric rats were prepared using multiple strains of ES cells as described below.

(1) Preparation of Blastocysts

Blastocysts obtained from a pregnant rat at 4.5 days of gestation were incubated in an injection culture medium (antibiotic-free YPAC culture medium) for 2 to 3 hours and then used for microinjection.

(2) Preparation of ES Cells 10 to 20 dome-like colonies of ES cells in Example 2 were collected using a glass tube and treated with Accutase for 5 minutes, after which they were dispersed into single cells in the injection culture medium. Next, the cells were transferred to 500 μL of the injection culture medium and incubated at room temperature for 30 to 60 minutes, after which the ES cells were centrifuged and transferred to the injection culture medium and covered with mineral oil (SIGMA Company).

(3) Injection of ES Cells into Blastocysts 10 to 15 ES cells were injected into blastocysts, and to restore the original state of the embryo, the blastocysts were incubated in the injection culture medium at 37° C. for 3 to 5 hours. 10 to 20 embryos were transplanted to the uterine horn of a pseudopregnant rat on day 3.5 of gestation. Chimeric rats were identified by coat color, and germline transmission was identified by the coat color of the F1 rats born as a result of mating chimeric rats, and by the Oct4-VENUS fluorescence of fetal germ cells. Genotyping was achieved by subjecting tail DNA to PCR.

Example 5

Verification of Germline Transmission Chimeric Rats and Method of Preparation Thereof Verification was performed for the utility of the YPAC injection method and germline transmission as described below.

(1) Preparation of Rat ES Reporter Cells (Cyan)

To monitor rat ES cells, 5 μg of pCAG-AmCyan1 was introduced into $3.2 \times 10^6$ TgWW1 cells (ES cells) using a Mouse ES Cell Nucreofector Kit (Amaxa Company); colonies of ES cells positive for CAG-AmCyan1/Oct4-VENUS emitting cyan/green fluorescence were collected using a glass tube and amplified without drug selection, and these were used as the monitor cells (TgWW1+C). Also, 10 μg of pOct4-Venus was introduced into to $2.4 \times 10^6$ LL cells (ES cells), and reporter ES cells (LL1+V) were prepared in the same manner.

Figures 1, 4:
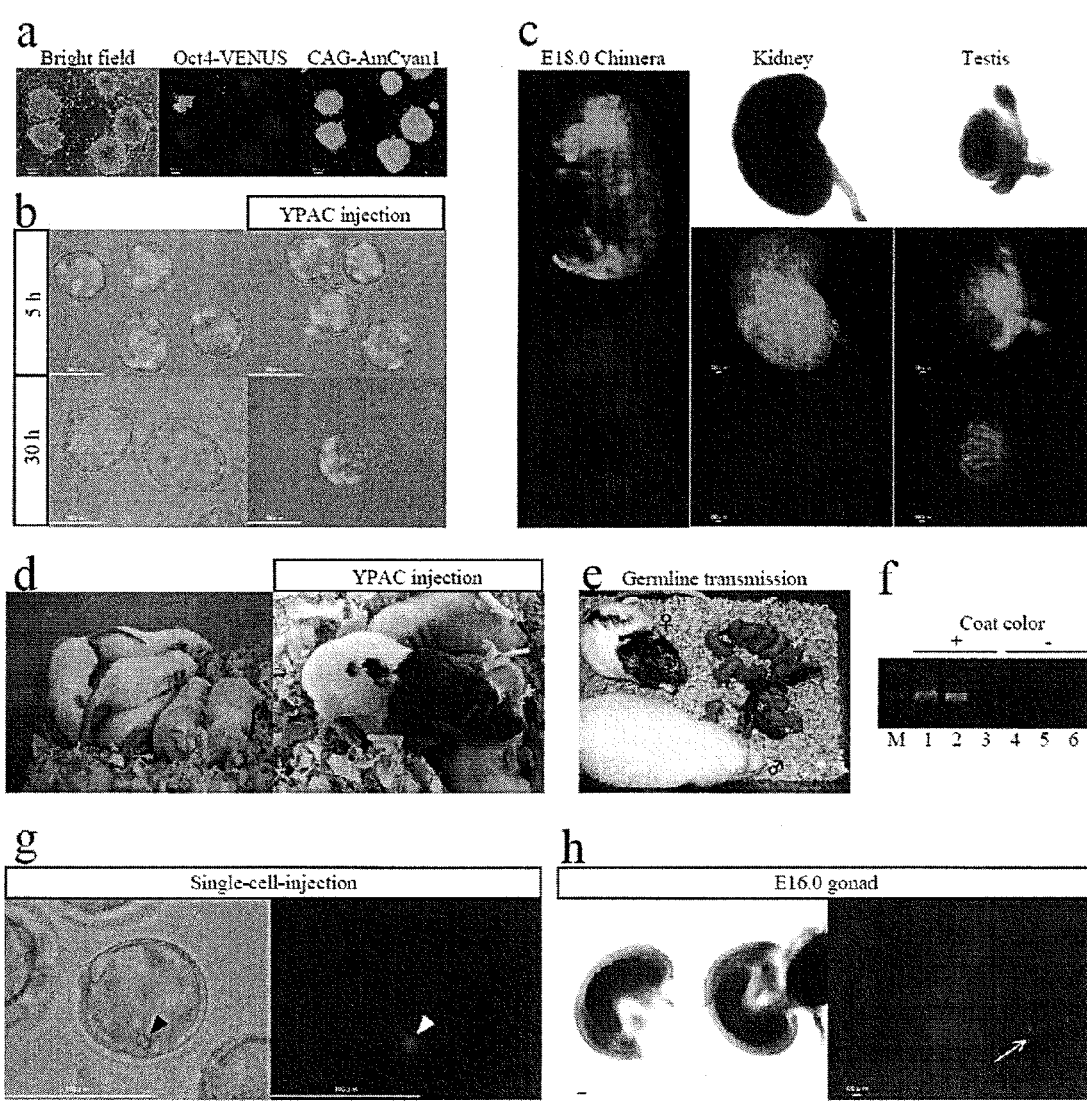

(2) Verification of Effect of Injection Culture Medium with Addition of the YPAC Factors An investigation was conducted with and without addition of the YPAC factors to the injection culture medium. After 5 hours of incubation, there was no difference between the results obtained with injection in the absence of the YPAC factors and those obtained with injection in the presence of the YPAC factors (hereinafter, referred to as "YPAC injection"); a wide variety of cyan-positive cells adhered onto the inner cell mass (ICM) and the trophic ectoderm (TE). However, after 30 hours of incubation in the absence of the YPAC factors, a small number of apoptosed cyan-positive cells were present in the blastocysts, whereas in the presence of the YPAC factors, some cells accumulated on ICM, and the shape of the blastocysts was maintained (FIG. 4b).

(3) Verification of Capability of Generating Germline Chimeric Rats

The ES cell TgWW1+C of Example 5(1) was injected into blastocysts and incubated for 3.5 hours, after which they were transferred to the uterus of a mouse at 3.5 days of pseudopregnancy. Two of the nine individuals at 18 days of embryo were found to be cyan-positive and negative for Oct4-Venus in the epidermis and kidney. Oct4-Venus-positive cells were detected specifically in germ cells on the gonad (FIG. 4c). For all other ES cells as well, the development of germline chimeras was confirmed by detecting Oct4-Venus fluorescence on the fetal gonad. Germline chimeras were identified in 2 of the 12 mice even in long cultured TgWL2 cells with 22 passages. Furthermore, germline transmission was also confirmed in LL1+V prepared by introducing the Oct4-Venus gene into LL cells induced from an LEA rat strain.

To identify chimeras by coat color, TgWL1 cells were injected into Wistar rats with addition of the YPAC factors. Of 23 individuals, 8 chimeric color rats developed from TgWL1 cells with a number of passages of 11 or 12 (FIG. 4d). Meanwhile, when the injection took place without addition of the YPAC factors, it was difficult to prepare a chimeric color rat, despite the use of the same cell line with a small number of passages of 6 or 8, with only 1 of 44 individuals being a chimeric color rat; the chimera ratio was low. The preparation of chimeric color rats using the YPAC factor was successful in all the 4 cell lines. To confirm germline transmission in F1, a TgWL1 chimera and a Wistar rat were mated; one individual of female chimeras produced 4 offspring individuals in agouti color out of 16 individuals containing germline transmission of the TgWL1 cell line (FIG. 4e). Also, F1 germline transmission was also confirmed in the cells derived from the TgWL2 cell line. It was found that, as shown in Table 2 and Table 3, when using the YPAC factors to prepare a chimeric rat, a germline-transmitted chimeric rat could be prepared without being limited by the strain of rat ES cells and the strain of host rat.

The cell lines used were TgWL1 and TgWL2, which were ES cells established from a TgWL rat (a hybrid between a transgenic Wistar rat and an LEA rat), TgWW1 and TgWW2, which were ES cells established from a TgWW rat (TgWW: a hybrid between a transgenic Wistar rat and a wild-type Wistar rat), WW1, which was an ES cell established from a WW rat (wild-type Wister rat), and LL1 and LL2, which were ES cells established from an LL rat (LEA rat).

To identify the Venus region by gene analysis, tail genomic DNA was collected and amplified by PCR. The Oct4-Venus gene of F0 chimera was inherited to 2 of 3 individuals of F1 germline with agouti color by Mendel's laws (FIG. 4f). When long-cultured ES cells (TgWL2: number of passages: 22) were injected into blastocysts, Venus fluorescence was detected on the gonad at 17.5 days of embryo, as shown in Table 2 (FIG. 4i).

Furthermore, the influences of the YPAC factors on chimera ratio were investigated. When chimeras were prepared without adding YPAC at the time of injection of TgWL1 rat ES cells (number of passages: 6) into blastocysts, and at the time of cultivation of the blastocysts (FIG. 4j), it was found that the agouti coat color chimera ratio was low, as indicated by the arrow in FIG. 4j. Meanwhile, a chimera of TgWW1 and LL1 ES cells was prepared in the presence of the YPAC factors (A: TgWW1 cells injected into LEA blastocysts; B: LL1 cells injected into Wistar blastocysts); it was found that the agouti coat color chimera ratio was high, as shown in FIG. 4k. The arrow in FIG. 4k indicates the degree of contribution of ES cells to the chimeras.

(4) Preparation of Germline Chimeras Derived from Single Rat ES Cells

To confirm the pluripotency of rat ES cells, single cells were injected into blastocysts (FIG. 4g). TgWW1 cells with a number of passages of 9 were injected into Wistar blastocysts, after which they were incubated using the YPAC factors injection medium for 3 hours to bind the single cells to the inner surface. Eight fetuses developed from 35 blastocysts at 16 days, with germline transmission achieved in 1 fetus (FIG. 4h).

(5) Investigation of Conditions of Preparation of Germline-Transmitted Chimeric Rats The results of an investigation of the preparation of chimeric rats using "the YPAC factors", which consisted of a ROCK inhibitor, an MEK inhibitor, a type I TGF-β receptor inhibitor, and a GSK3 inhibitor, or "the PAC factors", which consisted of 3 kinds of inhibitors, i.e., an MEK inhibitor (PD0325901), a type I TGF-β receptor inhibitor (A-83-01), and a GSK3 inhibitor (CHIR99021), are shown in Table 4. All rES cells were established using the YPAC culture medium.

The results of the investigation continued that it was possible to prepare a chimeric rat not only with the YPAC factors, but also with the PAC factors, and that the chimeric rat obtained had undergone germline transmission. Also, when the number of rES cells to be injected into host blastocysts is small, adding a ROCK inhibitor to the YPAC or PAC factors in the step of injecting an rES cell into a host embryo will increase the strength of adhesion of ES cells to blastocysts, and this was thought to be desirable.

Although preparation of chimeric animals using rat ES cells or mouse ES cells has been reported so far, no report is available on the addition of a compound that suppresses the differentiation of ES cells (MEK inhibitor, GSK3 inhibitor and the like) at the time of injection of the ES cells into a host embryo. The rat ES cells prepared in Example 1 are thought to possess the capability similar to that of rat ES cells described in a prior art document in that they are rat ES cells capable of germline transmission; however, under conditions without addition of an inhibitor, no germline-transmitted rat could be prepared. Therefore, it was found that the method of preparing a chimeric rat using a drug that suppresses the differentiation of ES cells makes it possible to much more efficiently prepare a germline-transmitted rat than the conventional method.

TABLE 2

| Cell line | Passage Number | Host blastocyst | Injected embryos | Fetal number | Germline[f] chimera[f] |
|---|---|---|---|---|---|
| TgWL2 | 6 | LEA | 43 | 9 | 1M1F[f] |
| | 22 | Wistar | 13 | 3 | 1F[f] |
| | | Wistar/LEA | 23 | 9 | 1F[f] |
| TgWW1 | 6, 7 | Wistar | 53 | 9 | 2M7F[f] |
| TgWW1 + C | 8 | Wistar | 46 | 9 | 1M1M or F[f] |
| TgWW1s | 9 | Wistar | 35 | 8 | 1F[f] |
| TgWW2[a] | 8 | Wistar | 28 | 1 | 1M[f] |
| LL1 + V | 9 | Wistar | 38 | 11 | 1F[f] |

ES cells were established using separate media.
M, male; F, female
TgWL: Wistar-LEA hybrid transgenic.
TgWW: Wistar-wild type Wistar hybrid transgenic
WW: Wild type Wistar
LL: LEA
TgWW1 + C indicates a cell line that stably expresses the expression of the transgene.
LL1 + V indicates a cell line that stably expresses the expression of the transgene Oct4-Venus.

TABLE 3

| Cell line (Sex) | Passage number | Host blastocyst | Injected embryos | Pups number | Chimera number | Mating number | Germline chimera |
|---|---|---|---|---|---|---|---|
| −YPAC injection | | | | | | | |
| TgWL1 (XX) | 6-8 | Wistar | 226 | 44 | 1M[a] | 0 | — |
| +YPAC injection | | | | | | | |
| TgWL1 (XX) | 11, 12 | Wistar | 123 | 23 | 3M5F | 1M3F | 1F |
| TgWL2 (XX) | 4, 6 | Wistar | 70 | 10 | 2M3F | 1M3F | 2F |
| TgWW1 (XX) | 9 | Wistar/LEA | 79 | 19 | 5M3F | 3F | 1F |
| WW1 (XX) | 10 | LEA | 27 | 7 | 2M1F | 1F | 1F |
| LL1 (XX) | 4, 6 | Wistar | 107 | 13 | 3F | 2F | 1F |
| LL2 (XX) | 9 | Wistar | 52 | 6 | 3F | 3F | 2F |

[a]The coat color range is narrow.

TABLE 4

| Cell line | Host blastocyst | Inhibitor | Germline chimera |
|---|---|---|---|
| TgWL1 | Wistar | — | NO |
|  | Wistar | Y | NO |
|  | Wistar | PAC | YES |
| TgWL2 | Wistar | PAC | YES |
|  | Wistar | YPAC | YES |
|  | LEA | YPAC | YES |
|  | Wistar/LEA | YPAC | YES |
| TgWW1 | Wistar | YPAC | YES |
|  | Wistar/LEA | YPAC | YES |
| TgWW2 | Wistar | YPAC | YES |
| TgLL1 | Wistar | YPAC | YES |

Example 6

Figure 5:
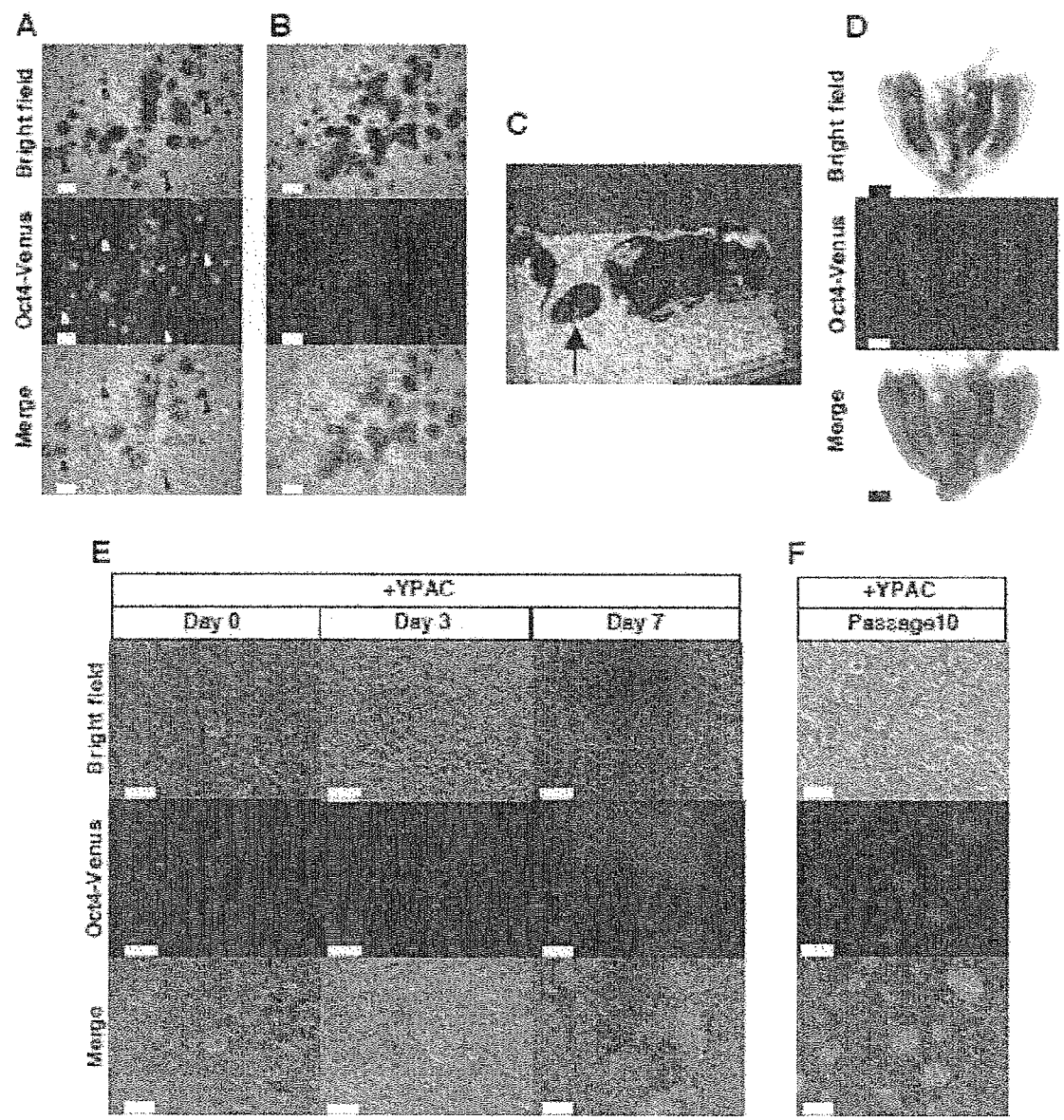
FIG. 5 is a graphic representation concerning the preparation of Tg rats from ES cells. (A) and (B) show the cloning and expression of Oct4-Venus transformant cells. The Oct4-Venus transgene was introduced into ES cells at 5 passages (LL2), and Venus-positive clones were subcultured without drug selection. The arrows in (A) indicate that Venus expression was suppressed. (B) shows the homogeneous expression of Oct4-Venus in ES cells. (C) shows Tg rats obtained from ES cells exhibiting the homogeneous expression of Oct4-Venus. The arrow indicates an esTG rat obtained from a chimeric rat via germline transmission. (D) shows Venus fluorescence on the gonad in an esTg rat at 16 days of embryo. (E) shows outgrowths of esTg blastocysts in YPAC culture medium. (F) shows a rat ES cell line derived from an esTg blastocyst. Suppression of the expression of Oct4-Venus was not observed even after 10 passages. (Scale bar: 300 μm (A, B, D), 100 μm (E, F)).

Preparation of Germline-Transmitted Chimeric Rat Derived from Genetically Modified ES Cells A germline-transmitted chimeric rat was prepared using genetically modified ES cells as described below.
(1) Preparation of Genetically Modified Rat ES Cells 10 μg of pOct4-Venus was introduced into 3×10$^6$ LL2 cells (ES cells established with the YPAC factors) using a Mouse ES Cell Nucleofector Kit (Amaxa Company) and seeded onto MEF in a culture vessel coated with 2% Matrigel (BD Bioscience Company). Colonies of Oct4-Venus-positive ES cells emitting green fluorescence were collected using a glass tube and amplified with drug selection, and they were used as the Oct4-Venus-positive ES cells (LL2). After 2 passages, the green fluorescence from 13 of the 15 ES cell colonies was uneven, whereas the other 2 emitted uniform fluorescence (FIGS. 5A, B).
(2) Preparation of Germline-Transmitted Chimeric Rat Derived from Genetically Modified ES Cells The ES cell LL2, which stably emits green fluorescence, was injected into Wister-derived blastocysts in the presence of the YPAC factors and incubated for 3-5 hours, after which it was transferred to the uterus of a mouse at 3.5 days of pseudopregnancy to yield a transgenic rat (esTG rat). Germline transmission in the prepared esTG rat was confirmed by the coat color of F1 rats (FIG. 5C, Table 3) and Venus fluorescence on the gonad of the esTG rat at 16 days of embryo (FIG. 5D). Also, the esTG rat grew while retaining the normal capability of reproduction.
(3) Verification of ES Cells Derived from the esTG Rat Verification was performed for the Venus fluorescence expression pattern of ES cells derived from the esTG rat. The Venus fluorescence expressed by outgrowths of blastocysts derived from the esTG rat (FIG. 5E) was the same as the outgrowths of blastocysts derived from the conventional transgenic rat prepared in Example 1 (cvTG) (FIG. 1b). Even after 10 passages, the cells were successfully cultured while stably maintaining the Venus fluorescence (FIG. 5F). Judging from these results, it was found that esTG rats of good quality that stably express Venus could be prepared.

Example 7

Preparation of Chimeric Rats Using Gene-Targeted Rat ES Cells

A ZFN pair that recognizes 124 bp downstream of the start codon in the first exon in the Oct4 gene was designed (Sigma Company), and a targeting donor configured with the short homology arm shown by FIG. 6A was prepared from rat genomic DNA by PCR using KOD Ver. 2 DNA polymerase (Toyobo).

Accurate targeting of this donor containing the AmCyan1-IRES-NEO cassette induced the expression of AmCyan1 and neomycin phosphotransferase under the control of the endogenous Oct4 promoter. 10 μg of the targeting donor and 5 μg of ZFN encoding mRNAs, along with a Mouse ES Cell Nucreofector kit (Amaxa Inc.), were added to 6×10$^6$ ES cells (Long-Evans Agouti (LEA), number of passages: 7) to achieve nucleofection. The ES cells were seeded onto MEF in a culture vessel coated with 2% Matrigel (BD Bioscience) and cultured in a culture medium supplemented with the YPAC factors without drug selection, and AmCyan1-positive cells were collected using a glass tube. There were no AmCyan-1-positive colonies with the donor alone inserted therein, and the expression of AmCyan1 was confirmed in 18 colonies incorporating both the ZFN encoding mRNA and the donor. These 18 colonies were subcultured, and 11 colonies survived. As a result of genotyping analysis, gene targeting was found to have been accurately achieved in 8 of the 11 clones (73%) (FIG. 6B).

These 8 hetero (Oct4+/−) clones exhibited uniform expression of AmCyan1 in undifferentiated cells but did not so in differentiated cells (FIG. 6C). For 4 clones that were amplified, 15 to 18 ES cells were injected with addition of the YPAC factors into blastocysts obtained from a pregnant rat at 4.5 days of gestation and transplanted to the uterine horn of a pseudopregnant rat at 3.5 days of gestation (species: Wister). Three coat color chimeras developed from 1 kind (No. 11) of clone.

Therefore, it was found that the rat ES cells established using the YPAC factors possess the capability of generating a chimeric rat even after undergoing a genetic modification such as gene targeting after establishment thereof.

TABLE 5

Development of chimeric rats from gene-targeted ES cell clones
Donor ES cells: Long-Evans Agouti (LEA)
Recipient blastocysts: Wister

| Clone No. | Passage number | Injected embryos | Pups number | Chimera number | Mating number |
|---|---|---|---|---|---|
| 10 | 14, 15, 17 | 117 | 23 | 0 | — |
| 11 | 14, 15 | 93 | 21 | 1M2F | 2F |
| 13 | 17-19 | 166 | 30 | 0 | — |
| 14 | 18, 19 | 62 | 11 | 0 | — |

Example 8

Preparation of p53 Gene Knockout Rats Using p53 Gene Deficient Rat ES Cells (p53$^{+/-}$)

(1) Preparation of p53 Gene Deficient Rat ES Cells (p53$^{+/-}$)

Figure 7:
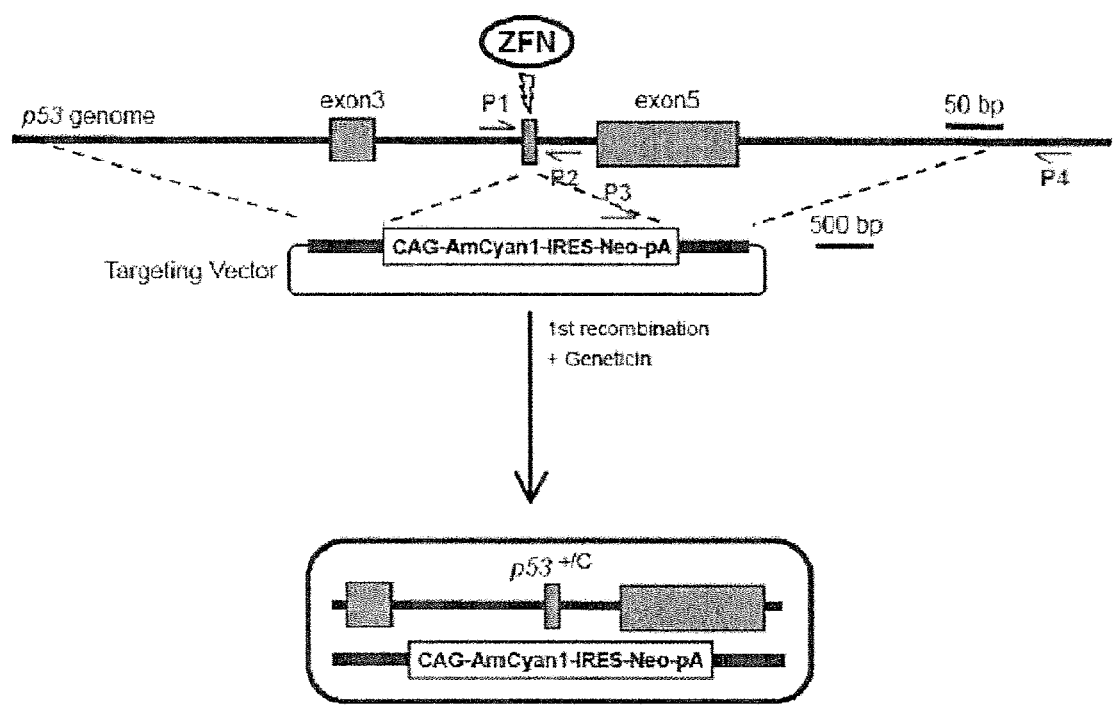
FIG. 7 is a graphic representation concerning the preparation of knockout rats by homologous recombination via ZFN. This is a schematic diagram concerning p53 targeting. The ZFN pair recognizes exon 4. The bald line indicates a homology arm.

A ZFN expression plasmid that recognizes the rat p53 gene (exon 4) and a ZFN encoding mRNA were designed (Sigma Company), and a targeting donor configured with the short homology arm shown by FIG. 7 was prepared from rat genomic DNA by PCR using KOD Ver. 2 DNA polymerase (Toyobo Co., Ltd.).

Figure 6:
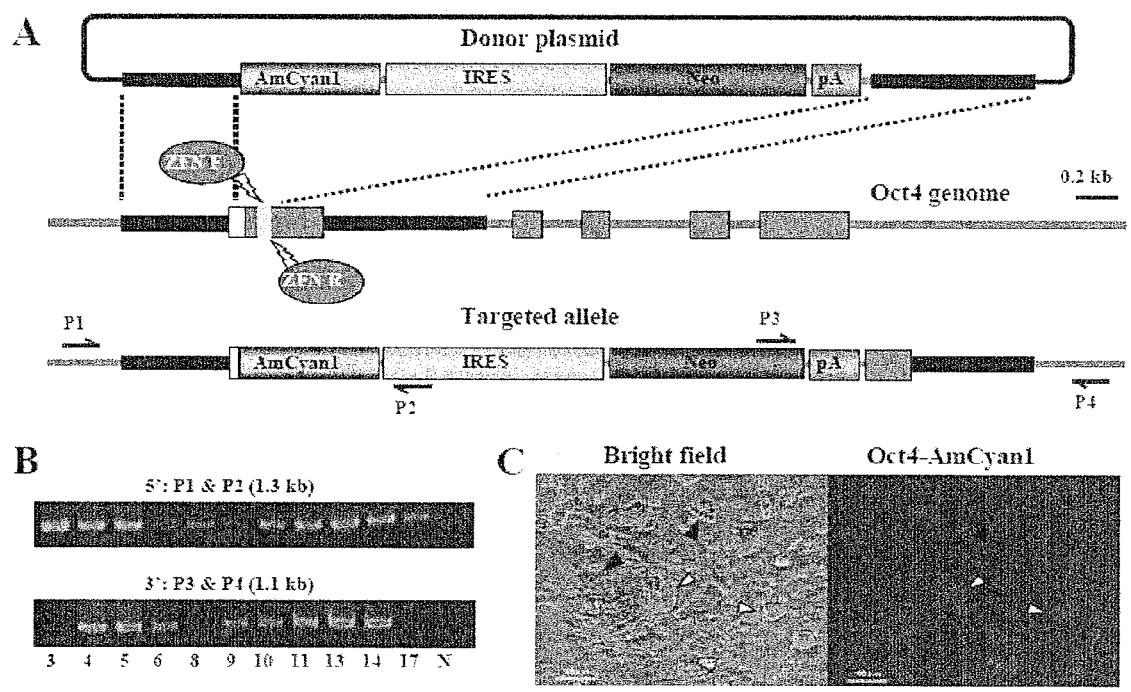
FIG. 6 is a graphic representation concerning the preparation of knockin rats by homologous recombination via ZFN. (A) is a schematic diagram concerning Oct4 targeting. The ZFN pair recognizes exon 1. Each gray box indicates a coding region, and each outlined box indicates a non-coding region. The bald line indicates a homology arm. Each P is a primer. (B) shows a genotyping PCR analysis of gene-targeted ES cell clones. (C) shows gene-targeted ES cell clone No. 11 (number of passages: 14) (outlined arrows: undifferentiated cells, solid arrows: differentiated cells).
Figure 8:
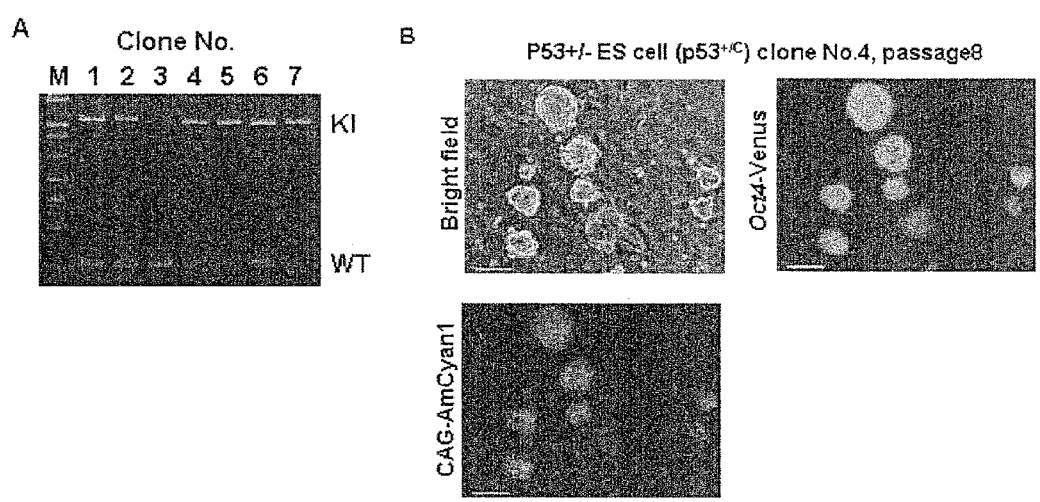
FIG. 8(A) shows a genotyping PCR analysis of gene-targeted ES cell clones (WT: wild type, KI: p53 gene-targeted alleles). (B) shows the expression of AmCyan1 in a homologously recombined p53$^{+/-}$ ES cell clone.

10 μg of the targeting donor and 5 μg of ZFN encoding mRNAs, along with a Mouse ES Cell Nucreofector kit (Amaxa Company), were added to 6.5×10$^5$ Oct4-Venus-positive ES cells established in Example 6(1) (LEA-strain rat) [LL2] (number of passages: 5) to achieve nucleofection. The ES cells were seeded onto MEF in a culture vessel coated with 2% Matrigel (BD Bioscience Company) and cultured in a culture medium supplemented with the YPAC factors. After 1 day of cultivation, Geneticin was added to the culture medium at a concentration of 0.2 µg/ml. At 11 days of cultivation, Geneticin-resistant ES cell colonies were collected into a glass tube and cultured. As a result of genotyping analysis, as shown in FIG. 8A, 6 colonies of the 7 colonies collected were found to have undergone homologous recombination, lacking the p53 gene (p53$^{+/-}$ ES cell). One colony (Clone No. 3) did not undergo homologous recombination. Cyan fluorescence also confirmed homologous recombination to the p53 gene locus in the p53$^{+/-}$ ES cells (FIG. 8B).

(2) Preparation of Chimeric Rats Using the p53 Gene Deficient Rat ES Cells (p53$^{-/-}$)

1 clone of the p53$^{+/-}$ ES cells found to have undergone homologous recombination (number of passages: 9) was injected into 90 blastocysts obtained from a Wistar-strain rat with addition of the YPAC factors (12 cells/1 blastocyst) and transplanted to the uterine horn of a pseudopregnant rat at 3.5 days of gestation (species: Wister). As a result, 9 of the 13 chimeric color rats (male chimeras: 5 individuals, female chimeras: 4 individuals) developed.

Figure 9:
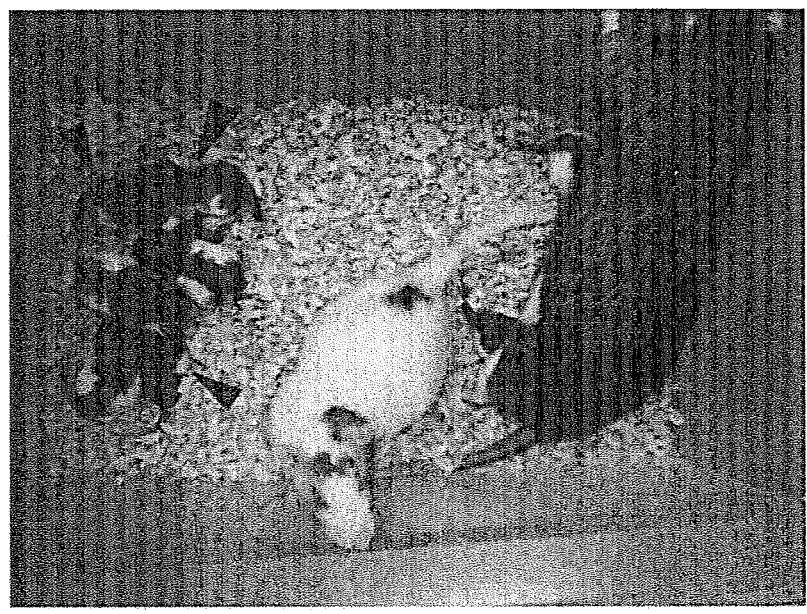
FIG. 9(A) shows p53 gene knockout rats obtained by mating a female chimera and a wild-type LEA-strain rat (the arrows indicate germline transmission rats). (B) shows a genotyping analysis of a rat generated as a result of mating of a female chimera and a wild-type LEA-strain rat (KI: p53 gene-targeted alleles).
Figure 9:
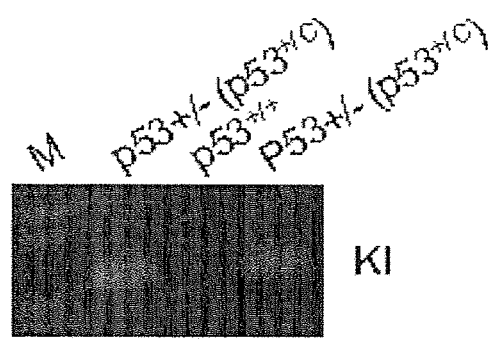

A female chimera and a wild-type LEA-strain rat were mated; of the liveborn rats, chimeric color rats were subjected to genotyping analysis; 2 of the 3 male chimeric color rats (rats with germline transmission) were found to have the p53 gene knocked out (p53$^{+/-}$) (FIG. 9).

Therefore, it was found that the rat ES cells established using the YPAC factors possess the capability of generating a chimeric rat even after undergoing a genetic modification such as gene targeting after establishment thereof, are capable of generating a chimeric rat with germline transmission, and are hence usable to prepare knockout rats.

Example 9

Preparation of Chimeric Rats Using the p53 Gene Deficient Rat ES Cells (p53$^{-/-}$)

(1) Preparation of p53 Gene Deficient Rat ES Cells (p53$^{+/-}$)

Figure 10:
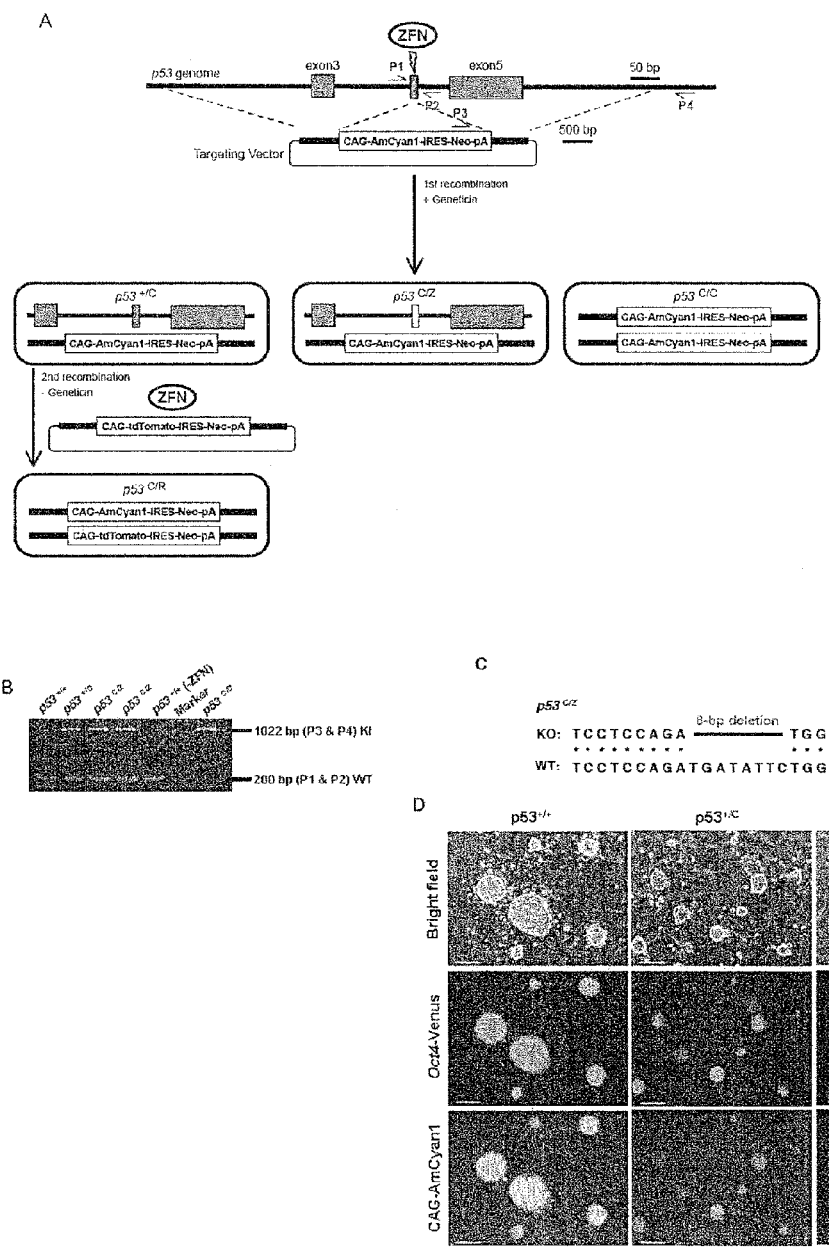
FIG. 10 is a graphic representation concerning the preparation of knockout rats by homologous recombination via ZFN. (A) is a schematic diagram concerning p53 targeting. The ZFN pair recognizes exon 4. The bald line indicates a homology arm. (B) shows a genotyping analysis of gene-targeted ES cell clones (WT: wild type, KI: p53 gene-targeted alleles). The lanes are numbered 1-7 from the left. (C) shows details of gene targeting of p53$^{-/-}$ ES cells [Cell Line: p53$^{C/Z}$]. (D) shows the expression of AmCyan1 in homologously recombined p53$^{+/-}$ ES cell clones.

A ZFN expression plasmid that recognizes the rat p53 gene (exon 4) and a ZFN encoding mRNA were designed (Sigma Company), and a targeting donor configured with the short homology arm shown by FIG. 10A (CAG-AmCyan1-IRES-Neo-pA) was prepared from rat genomic DNA by PCR using KOD Ver. 2 DNA polymerase (Toyobo Co., Ltd.).

10 µg of the targeting donor and 5 µg of ZFN encoding mRNAs, along with a Mouse ES Cell Nucreofector kit (Amaxa Company), were added to 4.5×10$^6$ Oct4-Venus-positive ES cells (Wistar-strain rat) (number of passages: 3) to achieve nucleofection. The ES cells were seeded onto MEF in a culture vessel coated with 2% Matrigel (BD Bioscience Company) and cultured in a culture medium supplemented with the YPAC factors. After 1 day of cultivation, Geneticin was added to the culture medium at a concentration of 0.2 µg/ml. At 9 days of cultivation, 46 Geneticin-resistant colonies were collected and cultured. As a result of genotyping analysis, p53 gene deficient ES cells that had undergone homologous recombination (p53$^{+/-}$ ES cells [Cell Line: p53$^{+/C}$]) were identified (FIG. 10B Lane 2, FIG. 10D). One of the 46 colonies was found to have undergone biallelic homologous recombination (p53$^{-/-}$ ES cells [Cell Line: p53$^{C/C}$]) (2.2%) (FIG. 10B Lane 7, FIG. 10D). Seven of the 46 colonies were found to have undergone monoallelic homologous recombination and a monoallelic frame shift (p53$^{-/-}$ ES cells [Cell Line: p53$^{C/Z}$]) (15%) (FIG. 10B Lanes 3 and 4, FIG. 10C, FIG. 10D). For control, 10 µg of the targeting donor alone was nucleofected to 4.5×10$^6$ Oct4-Venus-positive ES cells (Wistar-strain rat) (number of passages: 3). The ES cells were seeded onto MEF in a culture vessel coated with 2% Matrigel (BD Bioscience Company) and cultured in a culture medium supplemented with the YPAC factors. After 1 day of cultivation, Geneticin was added to the culture medium at a concentration of 0.2 µg/ml. At 9 days of cultivation, 14 Geneticin-resistant colonies were collected and cultured. As a result of genotyping analysis, it was found that these colonies had not undergone homologous recombination and had targeting donor integrated randomly therein (p53$^{+/+}$ ES cells [Cell Line: p53$^{+/+}$ (-ZFN)]) (FIG. 10B, Lane 5).

(2) Preparation of p53 Gene-Deficient Rat ES Cells (p53$^{-/-}$)

A ZFN expression plasmid that recognizes the rat p53 gene (exon 4) and a ZFN encoding mRNA were designed (Sigma Company), and a targeting donor configured with the short homology arm shown by FIG. 10A (containing tdTomato, in place of AmCyan1, as the reporter gene; CAG-tdTomato-IRES-Neo-pA) was prepared from rat genomic DNA by PCR using KOD Ver. 2 DNA polymerase (Toyobo Co., Ltd.).

Figure 11:
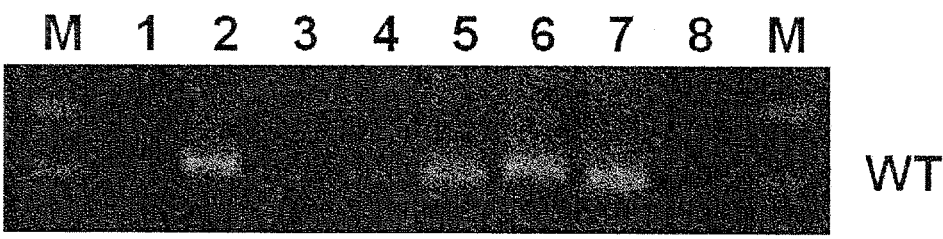
In FIG. 11, (A) shows a genotyping analysis of gene-targeted ES cell clones (WT: wild type). (B) shows the expression of AmCyan1 and tdTomato in a homologously recombined p53$^{-/-}$ ES cell clone.
Figure 11:
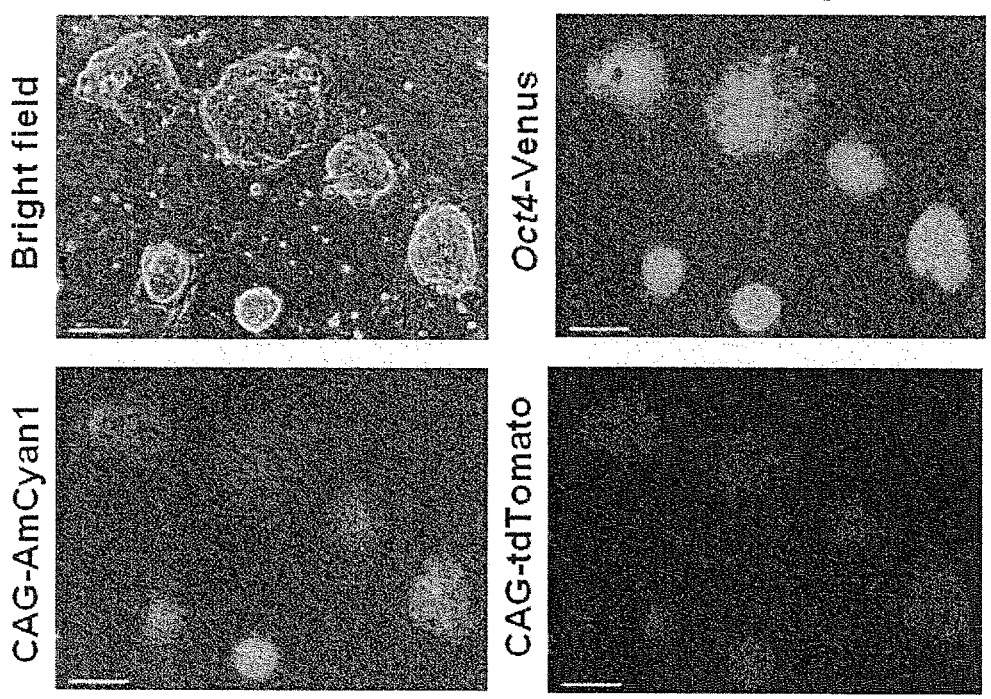

10 µg of the targeting donor and 5 µg of the ZFN encoding mRNAs, along with a Mouse ES Cell Nucreofector kit (Amaxa Company), were added to 2.5×10$^6$ p53$^{+/-}$ ES cells prepared in Example 9(1) [Cell Line: p53$^{+/C}$] (number of passages: 9) to achieve nucleofection. The ES cells were seeded onto MEF in a culture vessel coated with 2% Matrigel (BD Bioscience Company) and cultured in a culture medium supplemented with the YPAC factors. After 6 days of cultivation, 8 colonies expressing the red fluorescence of tdTomato were collected and cultured (FIG. 11B). As a result of genotyping analysis, 3 colonies (Clone Nos. 1, 3, and 8) were found to have undergone homologous recombination (38%) (p53$^{-/-}$ ES cells [Cell Line: p53$^{C/R}$]) (FIG. 11A).

(3) Preparation of Chimeric Rats Using the p53 Gene Deficient Rat ES Cells (p53$^{-/-}$) (p53$^{+/-}$)

The p53$^{+/-}$ ES cells prepared in Example 9(1) [Cell Line: p53$^{+/C}$] and the p53$^{-/-}$ ES cells prepared in Example 9(1) and (2) [Cell Lines: p53$^{C/C}$, p53$^{C/Z}$, p53$^{C/R}$], 12 ES cells each, were injected into blastocysts obtained from a pregnant rat at 4.5 days with addition of the YPAC factors and transplanted to the uterine horn of a pseudopregnant rat at 3.5 days of gestation (species: LEA).

As a result, when using the p53$^{+/-}$ ES cells, a coat color chimera emerged. Also, normal growth of chimeric rat fetuses was confirmed at high frequency, and the percent contribution of the p53$^{+/-}$ ES cells was also high.

Figure 12:
FIG. 12 shows (A) chimeric rat fetuses that developed from a p53$^{-/-}$ ES cell [Cell Line: p53$^{C/R2}$]. (B) shows the head malformation in a chimeric rat fetus (left in the figure) that developed from a p53$^{-/-}$ ES cell [Cell Line: p53$^{C/R2}$]. (C) shows the expression of AmCyan1 in the head of the fetus in (B).

Meanwhile, when using the p53$^{-/-}$ ES cells, malformations occurred in 184 of the 209 chimeric rat fetuses. These malformations were found in 6 clones of the p53$^{-/-}$ ES cells (FIG. 12). The chimeric rat fetuses with malformations mostly suffered abortion (FIG. 12A). Chimeric rat fetuses that developed from 2 clones of the p53$^{-/-}$ ES cells (p53$^{C/C1}$, p53$^{C/R2}$) had malformations in their heads (left in FIG. 12B). This phenotype, as confirmed by cyan fluorescence, is attributed to the high contribution of the p53$^{-/-}$ ES cells to the head (left in FIG. 12C). In 25 chimeric rat fetuses out of the 209 normally grown chimeric rat fetuses (right in FIG. 12B), the contribution of the p53$^{-/-}$ ES cells to the head was low (right in FIG. 12C). Abnormal growth of chimera occurred at considerably higher frequency when using the p53$^{-/-}$ ES cells (85.5±2.6%) than using the p53$^{+/-}$ ES cells (25.2±5.7%).

TABLE 6

Investigation of development of chimeric rats from various cell clones

| Genotype | Cell line | Injected embryos | Implanted embryos | Normal (%) | Abnormal (%) |
|---|---|---|---|---|---|
| p53$^{+/-}$ | p53$^{+/C1}$ | 54 | 17 | 11 (65) | 6 (35) |
| | p53$^{+/C2}$ | 176 | 41 | 35 (85) | 6 (15) |
| | p53$^{+/C3}$ | 27 | 12 | 9 (75) | 3 (25) |
| p53$^{-/-}$ | p53$^{C/C1}$ | 91 | 35 | 5 (14) | 30 (86) |
| | p53$^{C/21}$ | 124 | 61 | 7 (11) | 54 (89) |
| | p53$^{C/22}$ | 52 | 10 | 2 (20) | 8 (60) |
| | p53$^{C/R1}$ | 68 | 9 | 2 (22) | 7 (78) |
| | p53$^{C/R2}$ | 161 | 49 | 7 (14) | 42 (86) |
| | p53$^{C/R3}$ | 110 | 45 | 2 (4) | 43 (96) |

Therefore, it was found that the rat ES cells established using the YPAC factors possess the capability of generating a chimeric rat even after undergoing a genetic modification such as gene targeting in two cycles after establishment thereof.

Conventionally, because vast time and cost are taken to select genetically modified ES cells, monoallelically modified ES cells have been used to prepare a genetically modified animal with a biallelically modified desired gene. For this reason, there is absolutely no report on preparing a genetically modified animal by biallelically deleting the target gene in ES cells. In 2010, it was also reported that monoallelically deficient p53 knockout rats were born as a result of mating monoallelically deficient p53 knockout rats prepared from ES cells monoallelically deficient in the p53 gene (Nature vol. 467, 211-215(2010)), but it was not reported that any malformation occurred as described in Example 9 above.

As in the present invention, time taken to prepare a genetically modified animal can be shortened by biallelically modifying the target gene (gene destruction, mutations, and the like) to yield a genetically modified animal in the rat ES cell stage, so that a gene functional analysis at the individual level is thought to be speeded. It is also expected that the reliability and accuracy of the gene functional analysis will increase compared with conventional analysis, and that an animal model of disease more accurately reflecting the actual condition will be prepared.

INDUSTRIAL APPLICABILITY

By using the method of the present invention, irrespective of the strain of rat ES cell or the strain of host embryo, a chimeric embryo with improved germline transmission efficiency can be prepared; by using the chimeric embryo, a germline-transmitted chimeric rat can be prepared at high efficiency. Thereby it is possible to easily prepare genetically modified rats (knockout rats, knockin rats, and the like) that can be widely used for a wide variety of pharmacological or physiological studies, as well as for regenerative medicine studies and the like.

This application is based on a patent application Nos. 2009-274008 filed on Dec. 1, 2009 and 2010-166571 filed on Jul. 23, 2010 in Japan, the contents of which are incorporated in full herein.

The invention claimed is:

1. A method of preparing a chimeric embryo, comprising (a) a step for introducing a rat pluripotent stem cell into a fertilized host embryo collected from a female rat, wherein the introducing is in a medium comprising an ES cell differentiation suppressant comprising an MEK inhibitor, a GSK3 inhibitor, and a TGFβ receptor inhibitor, to produce a chimeric rat embryo.

2. The method according to claim 1, wherein the introducing is achieved by injecting the rat pluripotent stem cell into the host embryo.

3. The method according to claim 1, wherein the rat pluripotent stem cell is introduced into the host embryo in a medium comprising the ES cell differentiation suppressant of step (a) and a ROCK inhibitor.

4. The method according to claim 1, wherein the host embryo is precultured in a medium comprising the ES cell differentiation suppressant before introduction of the rat pluripotent stem cell.

5. The method according to claim 4, wherein the preculture is performed in a medium comprising the ES cell differentiation suppressant and a ROCK inhibitor.

6. The method according to claim 2, wherein the medium comprises the ES cell differentiation suppressant and a ROCK inhibitor.

7. The method according to claim 1, wherein the pluripotent stem cell is an ES cell.

8. The method according to claim 1, wherein the rat pluripotent stem cell is a pluripotent stem cell prepared from a rat of a strain that does not produce a germline-transmitted chimeric rat when introduced into a host embryo in the absence of the ES cell differentiation suppressant in the step (a).

9. The method according to claim 1, wherein the host embryo is derived from a rat of a strain that does not produce a germline-transmitted chimeric rat when introduced with a rat pluripotent stem cell in the absence of the ES cell differentiation suppressant in the step (a).

10. The method according to claim 1, further comprising (b) a step for culturing the chimeric embryo in a medium comprising the ES cell differentiation suppressant to form a chimeric blastocyst.

11. The method according to claim 10, wherein the medium of step (b) comprises the ES cell differentiation suppressant and a ROCK inhibitor.

12. A method of preparing a chimeric rat, comprising transplanting a chimeric blastocyst prepared by the method according to claim 10 to the uterus or oviduct of a psuedopregnant female rat to allow an offspring rat to be born.

13. A method of preparing a rat with a contribution of a rat pluripotent stem cell to the whole body, comprising mating a chimeric rat obtained by the method according to claim 12 with a rat of the opposite sex.

* * * * *